United States Patent
Howard, III

[11] Patent Number: 6,007,549
[45] Date of Patent: Dec. 28, 1999

[54] POSTERIOR BURR HOLE LOCALIZER

[75] Inventor: Matthew A. Howard, III, Iowa City, Iowa

[73] Assignee: The University of Iowa Research Foundation, Iowa City, Iowa

[21] Appl. No.: 08/874,325

[22] Filed: Jun. 13, 1997

[51] Int. Cl.[6] .................................................. A61B 19/00
[52] U.S. Cl. .......................................... 606/130; 602/74
[58] Field of Search .................................. 602/74; 2/171; 606/130

[56] References Cited

U.S. PATENT DOCUMENTS

| | | | |
|---|---|---|---|
| 488,802 | 12/1892 | Turner | 602/74 |
| 1,471,839 | 10/1923 | Epling | 602/74 |
| 3,053,256 | 9/1962 | Cooper et al. | |
| 3,223,087 | 12/1965 | Vladyka et al. | |
| 4,386,602 | 6/1983 | Sheldon et al. | |
| 4,397,307 | 8/1983 | Keller | |
| 4,613,324 | 9/1986 | Ghajar | |
| 4,860,331 | 8/1989 | Williams et al. | |
| 5,569,267 | 10/1996 | Howard, III et al. | |

FOREIGN PATENT DOCUMENTS

| | | | |
|---|---|---|---|
| 306638 | 2/1929 | United Kingdom | 602/74 |
| 2213066 | 8/1989 | United Kingdom | 606/130 |

OTHER PUBLICATIONS

A. Albright, M.D., et al.; "Function of parietal and frontal shunts in childhood hydrocephalus;" J. Neurosurg. vol. 69, Dec., 1988.

*Primary Examiner*—Michael Buiz
*Assistant Examiner*—Julian W. Woo
*Attorney, Agent, or Firm*—Fleshner & Kim

[57] ABSTRACT

A posterior burr hole Vocalizer device comprises a head band for attachment to a patient's head, a band constriction unit for adjusting the diameter of the head band, a sagittal plane aligning piece, and a trajectory plane aligning piece. The device is properly positioned on a patient's head in relation to the supraorbital rims and the superior attachment point of the patient's external ears in order to define an optimum location for a posterior burr hole site. Methods of making such a burr hole localizer device are also disclosed, together with methods for locating an anterior target site and an optimum posterior burr hole site.

20 Claims, 18 Drawing Sheets

POSTERIOR BURR HOLE LOCALIZER

BACKGROUND OF THE INVENTION

1. Field of the Invention

This invention relates to a burr hole localizer device for attachment to the head of a patient in order to facilitate localization of an optimum site for posterior burr hole placement, and methods of making such a device. This invention also relates to methods of locating an optimal site for a posterior burr hole prior to a parieto-occipital shunt operation.

2. Background of the Related Art

Ventriculoperitoneal (VP) shunt placement for hydrocephalus is one of the most common procedures in neurological surgery. Hydrocephalus may result from subarachnoid hemorrhage, trauma, tumors, and the like. The technique entails introducing a catheter through brain tissue into one of the lateral ventricles of the brain. Cerebrospinal fluid in the ventricle may be vented through the catheter to relieve signs, symptoms, and sequelae of hydrocephalus.

The current surgical technique for placement of VP shunts was developed in the 1950's by Scarff and has persisted with few modifications. Despite the relative simplicity of this procedure, the complication rate can be significant and includes operative morbidity as well as post-operative infections and obstructions, etc. Surgical technique plays a major role in reducing complications associated with VP shunts. Improper placement of the ventricular catheter may result in neurologic injury from the misplaced catheter or may cause an early proximal shunt obstruction, which is often secondary to blockage by adherent choroid plexus and other debris. The incidence of misplaced catheters is variable and dependent on a variety of factors, including the experience of the surgeon, the size of the targeted ventricle, the surgical approach, and the use of intraoperative guidance, such as fluoroscopy, ultrasound, or endoscopy. Thus, to optimize shunt function and minimize morbidity, proper placement of the proximal catheter is essential.

Two surgical approaches may be used for VP shunt placement, frontal and parietooccipital. Although little data is available, a retrospective series by Albright, et al., *J. Neurosurg.* 69:883–886 (1988), found good catheter placement in only 55% of frontal shunts and 33% of parieto-occipital shunts. Four cases of ophthalmic injury following ventricular catheter insertion were recently reported, and intracerebral hemorrhages secondary to misplacement have appeared in isolated clinical reports. The rate of such complications is not known. Recently, endoscopic placement of ventricular catheters has been reported with an accurate placement rate of 90%. *Neuroendoscopy:* Volume 1, Mary Ann Liebert, New York, pp. 29–40 (1992). The disadvantages of this technique are related to the cost of the instrumentation, the added operative time, and the time required for the surgeon to become familiar with the technique. If, however, an accurate, rapid, and inexpensive tool were available to aid in catheter placement, it would simplify the procedure.

A frontal catheter guide fulfilling these criteria has been successfully developed by Ghajar for placement of frontal ventricular catheters. Ghajar, J. B. G., A guide for ventricular catheter placement: technical note. *J. Neurosurgery*, 63:985–986, 1985. This instrument capitalized on the anatomical observation that a line passing perpendicular to the skull at the coronal suture will intersect the lateral ventricle.

However, parieto-occipital catheter placement has significant advantages over frontal catheter placement. The catheter path necessary for the frontal approach to the ventricles traverses frontal lobe regions having a low seizure threshold. Mechanical irritation of the neural tissue surrounding the catheter may give rise to epileptogenic foci independent of the underlying cause of hydrocephalus. This complicates patient management and increases health care costs, as well as markedly impacting the patient's quality of life.

The anatomy of the head and neck also causes technical difficulties for the surgeon. The distal end of the shunt is subcutaneously tunneled to the peritoneal cavity for implantation. Implantation in the open peritoneum provides an outlet for excess fluid drainage from the ventricles. The catheter path to the abdomen is circuitous from the frontal burr hole, however. The tube must pass posterior to the ear, and generally requires an additional skin incision. These difficulties increase operative time, cost, and complications.

In view of the above considerations, posterior shunt operations are often preferred over frontal shunt procedures (see, for example, J. L. Leggate, et al., J. Neurosurg., 68: 318–319 (1988)). In performing a posterior shunt operation according to the prior art, a catheter is passed from a posterior burr hole towards a frontal or anterior target point on the patient's forehead. Evidently, selection of an appropriate burr hole site is crucial to correct placement of a catheter within the target region (anterior horn of lateral ventricle) of the patient's brain. Notwithstanding, prior to the instant invention, there have been no mechanical or other forms of devices available to aid in the appropriate localization or selection of a posterior burr hole site. Indeed, the current standard practice is to palpate landmarks such as the external occipital protuberance, and to visualize where the burr hole should be located. This procedure is inherently inaccurate, and may result in severe neurologic injury when a catheter passed through a misplaced burr hole inadvertently traverses a critical brain structure (internal capsule).

Other than burr hole site selection, a second source of error in catheter placement during a posterior shunt procedure is insertion of the catheter along an incorrect trajectory. A simple mechanical device, known as the Caroline Guide, which eliminates this second source of error is taught by Howard III, et al. in U.S. Pat. No. 5,569,267, the contents of which are incorporated herein in their entirety.

The above references are incorporated by reference herein where appropriate for appropriate teachings of additional or alternative details, features and/or technical background.

SUMMARY OF THE INVENTION

An object, therefore, of the invention is to provide a posterior burr hole localizer for defining an optimum location for a posterior burr hole.

Another object of the invention is to provide a posterior burr hole localizer having an adjustable head band which can accommodate a wide range of different head sizes.

Another object of the invention is to provide a posterior burr hole localizer which is quick and simple to operate and which is inexpensive to manufacture.

Another object of the invention is to provide a method for making a posterior burr hole localizer for defining an optimum location for a posterior burr hole.

Another object of the invention is to provide a method for making a posterior burr hole localizer having an adjustable head band, a trajectory plane sighting slot, and a sagittal plane sighting slot which intersects the trajectory plane sighting slot.

Another object of the invention is to provide a method for locating an anterior target point on a patient's forehead.

Another object of the invention is to provide a method for locating an optimum site for a posterior burr hole in the occipito-parietal region of a patient's skull.

One advantage of the invention is that it provides a simple mechanical device and method for making a device that can be used to accurately and reproducibly locate an optimum site for a posterior burr hole prior to a posterior shunt procedure.

Another advantage of the invention is that it provides a method for accurately and reproducibly locating an optimum site for a posterior burr hole prior to a posterior shunt procedure.

Another advantage of the invention is that it provides a method for locating an anterior target site on a patient's forehead, preliminary to a posterior shunt operation.

One feature of the invention is that it provides a posterior burr hole localizer device for accurately and reproducibly locating an optimum site for a posterior burr hole.

Another feature of the invention is that it provides a posterior burr hole localizer featuring an adjustable head band, right and left ear spacers, a trajectory plane aligning piece, and a sagittal plane sighting piece.

Another feature of the invention is that it provides a quick and reliable method for locating an optimum location for a posterior burr hole site.

Another feature of the invention is that it provides a quick and reliable method for locating an anterior target site on a patient's forehead.

These and other objects, advantages and features are accomplished by the provision of a posterior burr hole localizer for locating a posterior burr hole site, including: a head band including right and left ear spacers, an anterior midpoint, and a posterior midpoint, the anterior midpoint having an anterior midpoint eyelet located thereat; a band constriction unit having a left side and a right side, the band constriction unit attached to the posterior midpoint of the head band; a trajectory plane aligning piece attached bilaterally to the head band; and a sagittal plane sighting piece attached to the right side of the band constriction unit. The right and left ear spacers may have respective right and left lower edges for location adjacent to the superior attachment point of the right and left external ears, respectively. The anterior midpoint eyelet defines an anterior target site when the posterior burr hole localizer is properly positioned on the head of a patient. The band constriction unit may be attached to the posterior midpoint of the head band. The trajectory plane aligning piece may have a trajectory plane sighting slot defining a region on a trajectory plane for correct catheter placement. The sagittal plane sighting piece may include a sagittal plane sighting slot that defines a sagittal plane located 3 cm to the right of the posterior midline. Further, the sagittal plane sighting slot may intersect with the trajectory plane sighting slot to provide a point of intersection.

These and other objects, advantages and features are further accomplished by the provision of a method for making a posterior burr hole localizer for attachment to a patient's head, including the steps of: providing a head band including an anterior midpoint, a posterior midpoint, and right and left ear spacers; forming an anterior midpoint eyelet in the anterior midpoint of the head band; attaching a trajectory plane aligning piece to the head band, the trajectory plane aligning piece having a trajectory plane sighting slot therein, wherein the trajectory plane sighting slot is located such that the trajectory plane sighting slot invariably defines a region of a trajectory plane for correct catheter placement when the posterior burr hole localizer is properly positioned on a patient's head; securing a band constriction unit to the posterior midpoint of the head band; and affixing a sagittal plane sighting piece to the band constriction unit, wherein the sagittal plane sighting piece includes a sagittal plane sighting slot, and wherein the sagittal plane sighting slot is located at a distance of approximately 3 cm. to the right of the posterior midpoint of the head band.

These and other objects, advantages and features are further accomplished by the provision of a method for locating an anterior target point on a patient's forehead, including the steps of: placing a frontal target localizing device against the inferior aspect of the patient's forehead; aligning a midline localizing unit of the frontal target localizing device with the anterior midline of the patient's nasal bridge at a distance approximately 2 cm. above the supraorbital rims of the patient's forehead; and marking the anterior target point on the patient's forehead at a point defined by the midline localizing hole.

These and other objects, advantages and features are further accomplished by the provision of a method for locating an anterior target point on a patient's forehead, including the steps of: a) placing a frontal target localizing device against the inferior aspect of the patient's forehead, the frontal target localizing device including: a plate having first and second sides, a midline localizing unit, a basal perimeter, and first and second supraorbital rim tabs extending away from the front plate at the basal perimeter; b) aligning the midline localizing unit with the anterior midline of the patient's nasal bridge; c) coincidentally with the step b), positioning the first and second supraorbital rim tabs flush with the supraorbital rims of the patient's forehead; and d) marking the anterior target point on the patient's forehead at a point defined by the midline localizing unit.

These and other objects, advantages and features are further accomplished by the provision of a method for locating an optimum location for a posterior burr hole, including the steps of: locating an anterior target point on the patient's forehead; marking an anterior target point on the patient's forehead; placing a posterior burr hole localizer on the patient's head, wherein the posterior burr hole localizer includes: an anterior midpoint eyelet; right and left ear spacers having right ear spacer lower edge and left ear spacer lower edge, respectively; a sagittal plane sighting piece having a sagittal plane sighting slot; and a trajectory plane aligning piece having a trajectory plane sighting slot, a and wherein the sagittal plane sighting slot and the trajectory plane sighting slot intersect to provide a point of intersection; properly positioning the posterior burr hole localizer on the patient's head such that the anterior midpoint eyelet is aligned with the anterior target point marked on the patient's forehead, and such that, coincidentally, the right ear spacer lower edge and left ear spacer lower edge are adjacent to the superior attachment point of the right external ear and the left external ear, respectively; and marking the point of intersection of the sagittal plane sighting slot and the trajectory plane sighting slot to locate the optimum location for the posterior burr hole.

These and other objects, advantages and features are further accomplished by the provision of a storage rack for holding a posterior burr hole localizer, including: an elongate member having a first end and a second end; a cross piece attached to the elongate member at the first end, wherein the cross piece includes an eyelet docking post extending along the longitudinal axis of the elongate member; a clip attached to the elongate member; a knob holder attached to the elongate member at the second end, the knob holder for accommodating a band tightening knob; and a sagittal plane sighting slot alignment indicator attached to the elongate member at a point on the elongate member between the knob holder and the clip.

The instant invention provides a relatively simple mechanical device for posterior burr hole localization, which can be manufactured inexpensively and can be adjusted to a range of different sizes to fit almost any adult patient. Use of the device adds only about a minute to the time required for a posterior shunt procedure and eliminates a major source of error in catheter placement. Additional advantages and features of the posterior burr hole localizer device and methods will become readily apparent from the following account thereof.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

Figure 1A:
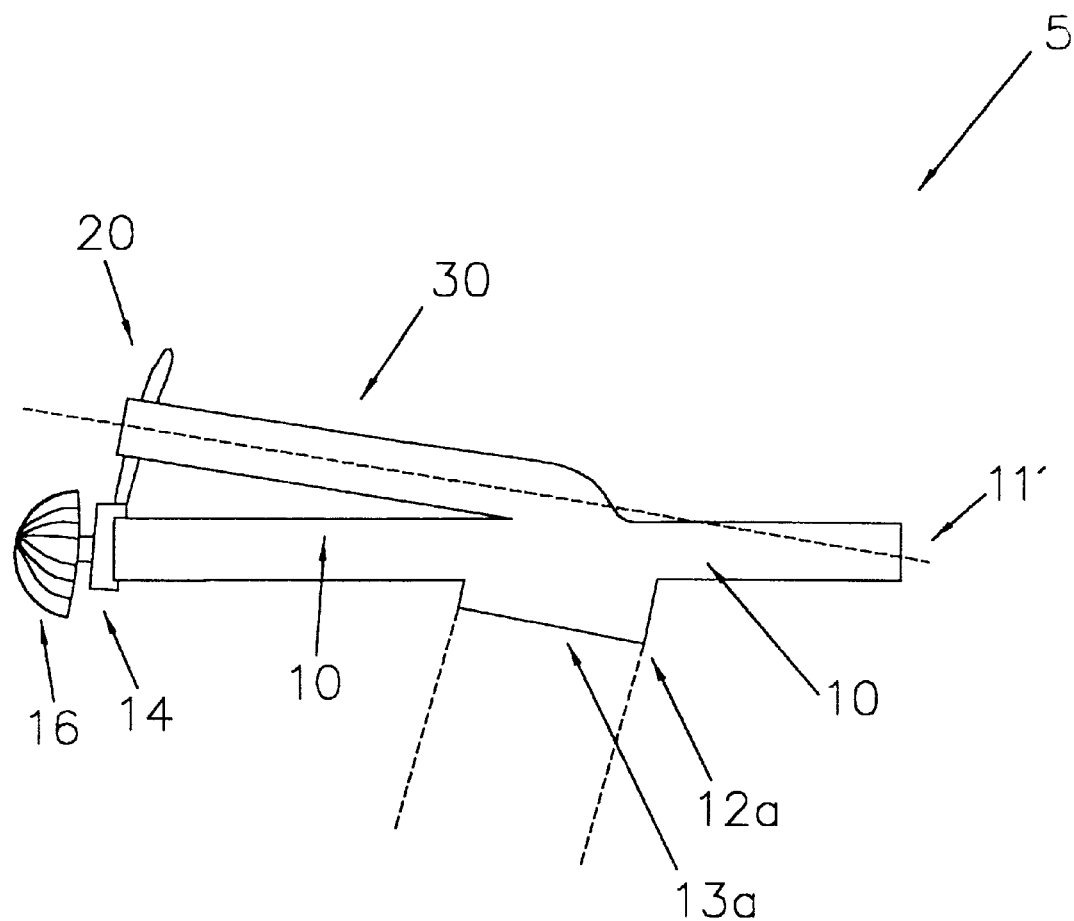
FIG. 1A is a side view of a posterior burr hole localizer.

The instant invention provides a posterior burr hole localizer in the form of a device which is relatively simple in its design and operation, and which can accurately and reproducibly identify an optimal site for a posterior burr hole for posterior ventricular catheter shunt procedures. The posterior burr hole localizer of the invention may be referred to as the Delia Localizer herein and elsewhere. The posterior burr hole localizer of the instant invention relies on the consistent anatomical relationship between the supra-orbital rims, the superior attachment point of the external ears, and the lateral cerebral ventricles; the latter representing the target site of the catheter during posterior shunt operations. The posterior burr hole site is represented by a point on the right occipital bone having two geometric characteristics: i) it is located approximately 3 cm. lateral to the right of the posterior midline; and ii) a line extending forward from that point to a frontal or anterior target point passes a distance of approximately 4 cm. above the superior attachment point of the external ear. The frontal target point is located at the anterior midline a distance of about 2 cm. above the supraorbital rims.

Referring now to the drawings, FIGS. 1A–1D show a side view of a posterior burr hole localizer 5, according to the invention. Posterior burr hole localizer 5 includes a head band 10 of variable size, the circumference of which may be conveniently adjusted by means of band constriction unit 14. That is to say, band constriction unit 14 provides for both constriction (decreasing the circumference) and expansion (increasing the circumference) of head band 10. Band constriction unit 14 has band constriction unit right hand side 14a and band constriction unit left hand side 14b, respectively. According to the invention, band constriction unit 14 may operate in conjunction with band tightening control 16. In accordance with a currently preferred embodiment, band tightening control 16 may take the form of a posteriorly mounted band tightening/releasing knob which may be operated by rotation clockwise or counterclockwise in order to adjust the circumference of head band 10.

Head band 10 includes anterior midpoint 11' and posterior midpoint 15 which are located diametrically opposite or 180 degrees from each other. Band constriction unit 14 and band tightening control 16 are located adjacent to posterior midpoint 15 of head band 10, and allow for constriction and expansion of head band 10, i.e. the circumference of head band 10 may be increased when band tightening control 16 is turned in a first direction and decreased when band tightening control 16 is turned in a second direction. Band tightening control 16, in conjunction with band constriction unit 14, has a self-locking function, i.e. the circumference of head band 10 is fixed or locked while band tightening control 16 is not rotated. In this way, a wide range of different head sizes can be accommodated by posterior burr hole localizer 5. Band tightening control 16 may include a locking unit (not shown) to prevent band tightening control 16 from being rotated inadvertently.

Head band 10 may take the form of a circular or substantially circular band of flexible to rigid material, which may include flexible or somewhat rigid plastic, or metal, or other suitable material. A preferred material for head band 10 is flexible plastic, such as a suitable form of PVC, polypropylene, and the like. Preferably the width of head band 10 ranges from about 1 cm. to about 7 cm. More preferably, head band 10 has a width of about 2 cm.

Figure 4A:
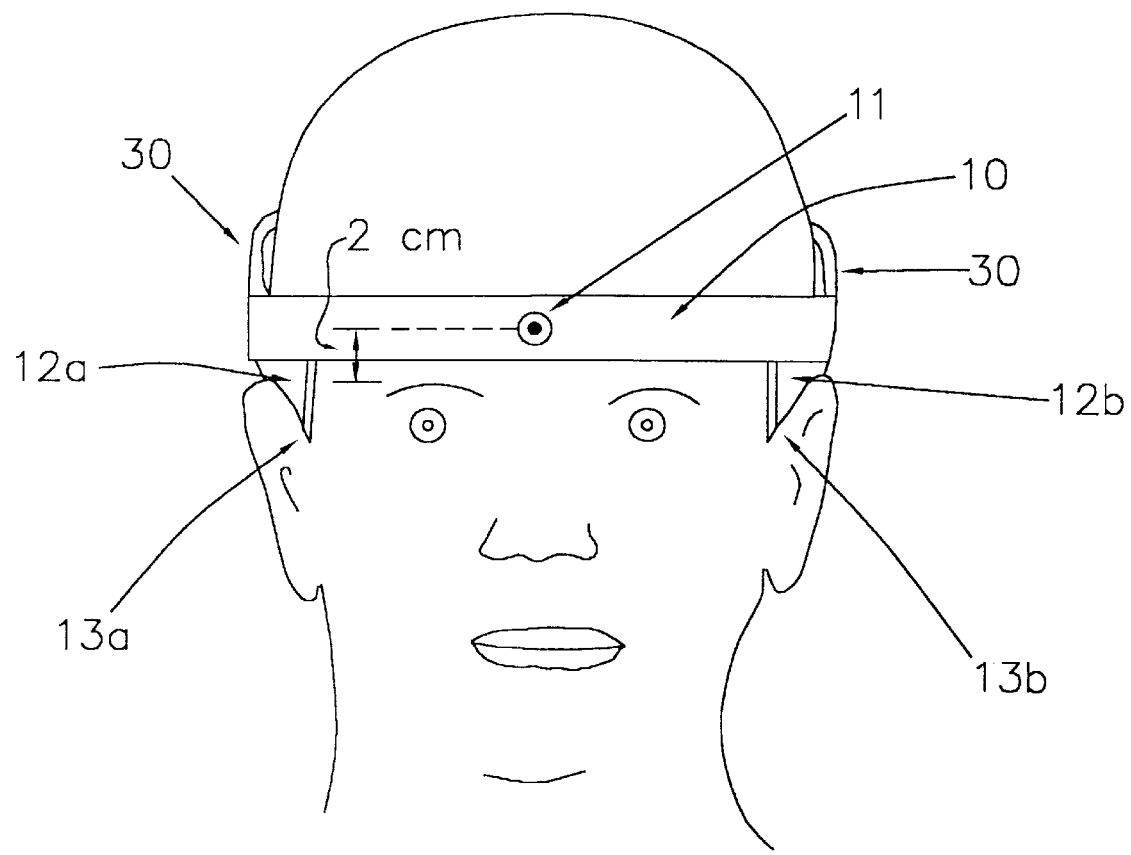
FIG. 4A is a front view of a posterior burr hole localizer attached to a patient's head showing the location of the anterior midpoint eyelet.
Figure 4B:
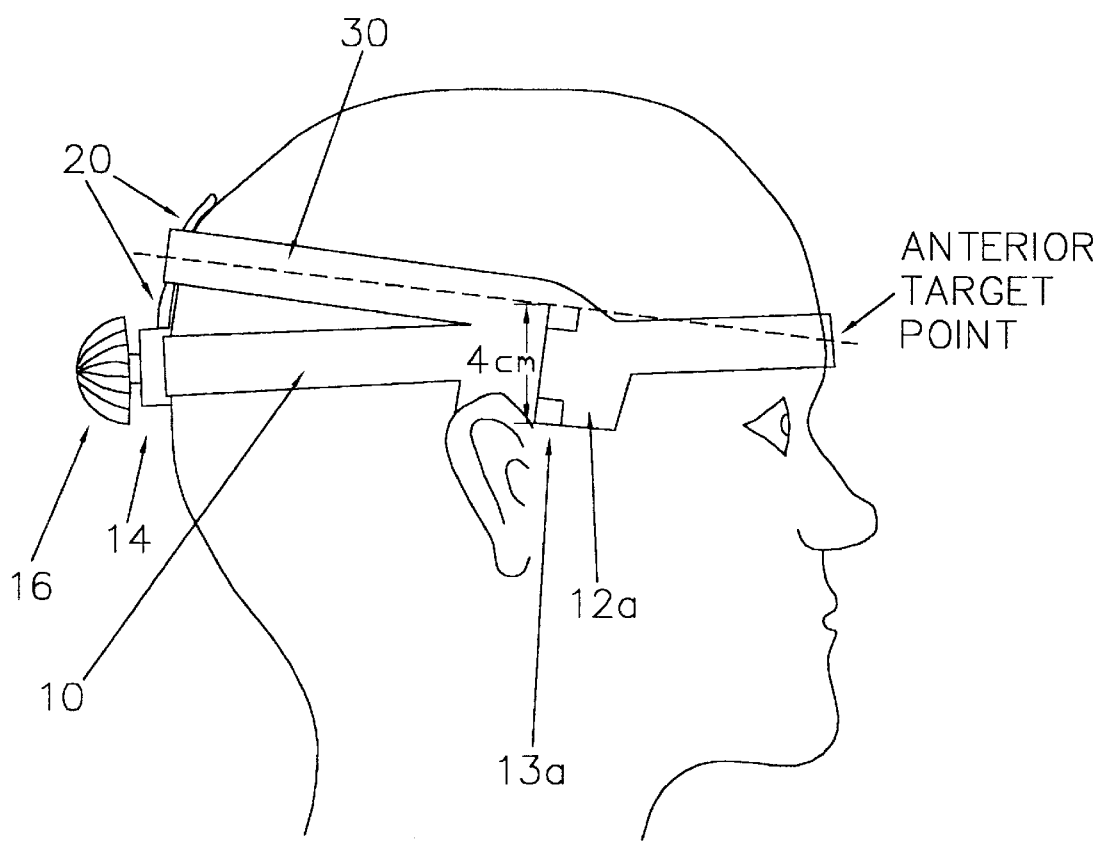
FIG. 4B is a side view of a posterior burr hole localizer attached to a patient's head as seen from the right hand side of the patient and showing the position of the right ear spacer in relation to the superior attachment point of the right external ear.

Posterior burr hole localizer 5 further includes a trajectory plane aligning piece 30 having a trajectory plane sighting slot 31, and a pair of bilateral ear spacers, namely right and left ear spacers 12a,b, respectively. Right and left ear spacers 12a,b are attached to head band 10, and include right and left ear spacer lower edges 13a,b, respectively. Posterior burr hole localizer 5 takes advantage of the reliable anatomical relationship between the superior attachment point of the external ears and the cerebral ventricle, whereby the trajectory plane for correct catheter placement is located approximately 4 cm. above the superior attachment point of the external ears along a line normal to the trajectory plane. When posterior burr hole localizer 5 is properly positioned on the patient's head, right and left ear spacer lower edges 13a,b are adjacent to the superior attachment point of the patient's respective right and left external ears (FIG. 4B). Regardless of the circumference to which head band 10 is adjusted, when posterior burr hole localizer 5 is properly positioned on a patient's head, right and left ear spacer lower edges 13a,b are arranged parallel to a line representing the trajectory plane for correct catheter placement. Consequently, posterior burr hole localizer 5 is capable of accommodating a range of different head sizes. The trajectory plane for correct catheter placement is represented by the dashed line in FIG. 1A (and in FIG. 4B). Posterior No burr hole localizer 5 has trajectory plane sighting slot 31 and right and left ear spacer lower edges 13a,b oriented with respect to each other such that when localizer 5 is properly positioned on the patient's head, trajectory plane sighting slot 31 is aligned with the trajectory plane for correct catheter placement, represented by the dashed line in FIG. 1A (and in FIG. 4B). Since right and left ear spacer lower edges 13a,b are arranged parallel to a line representing the trajectory plane for correct catheter placement, the trajectory plane is located approximately 4 cm. above the superior attachment point of the external ears along a line normal to right and left ear spacer lower edges 13a,b.

Posterior burr hole localizer 5 further includes a sagittal plane sighting piece 20 which extends substantially vertically adjacent to the back of the skull (occipito-parietal), and is attached to the right hand side 14a of band constriction unit 14 such that sagittal plane sighting piece 20 lies adjacent to the sagittal plane at a typical distance of about 3 cm. to the right of the posterior midline.

Sagittal plane sighting piece 20 includes a sagittal plane sighting slot 21 which, according to a preferred embodiment of the invention, may take the form of an elongated opening, within sagittal plane sighting piece 20, oriented in the longitudinal direction. Sagittal plane sighting slot 21 defines a first coordinate of a posterior burr hole site, and is located at a distance of between 1.5 and 3.5 cm. to the right of posterior midpoint 15 of head band 10. Preferably, sagittal plane sighting slot 21 is located at a distance of about 3 cm. to the right of posterior midpoint 15 of head band 10. Sagittal plane sighting slot 21 is located within sagittal plane sighting piece 20 of posterior burr hole localizer 5 in such a manner that, when posterior burr hole localizer 5 is properly positioned on the patient's head, sagittal plane sighting slot 21 invariably defines the sagittal plane at a distance of about 3 cm. to the right of the posterior midline.

Figure 2:
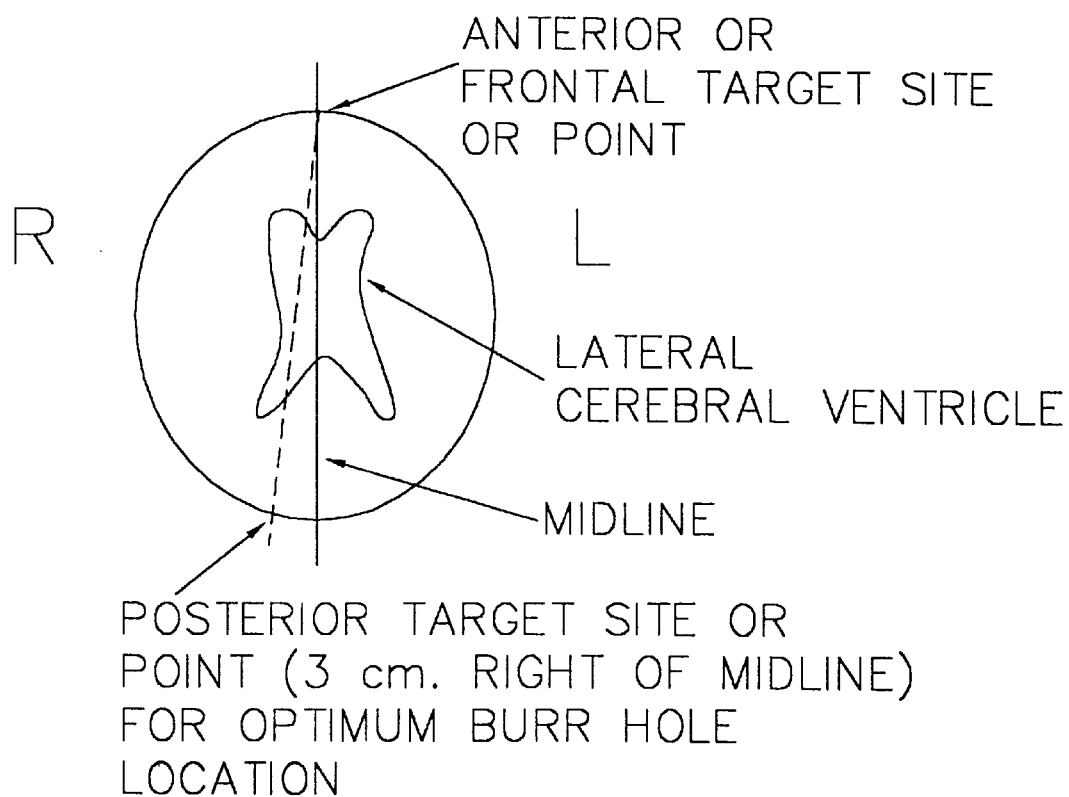
FIG. 2 shows the projected catheter trajectory as a dashed line superimposed on an axial CT scan image of the patient prepared prior to burr hole localization and catheter placement.

Trajectory plane aligning piece 30 is also attached to head band 10; and preferably trajectory plane aligning piece 30 is attached bilaterally to, or on each side of, head band 10. Trajectory plane aligning piece 30 may be integral with head band 10, or alternatively trajectory plane aligning piece 30 may be formed as a separate component which is subsequently attached to head band 10. According to a preferred embodiment, trajectory plane aligning piece 30 is attached bilaterally to head band 10 at a point substantially above each ear spacer 12a, 12b. Trajectory plane aligning piece 30 includes trajectory plane sighting slot 31 which, according to a preferred embodiment of the invention, may take the form of an elongated opening within trajectory plane aligning piece 30, the opening oriented in the latitudinal direction. The trajectory plane corresponding to correct catheter insertion is defined by a straight line joining the anterior target point or site, located at the anterior midline 2 cm. above the supraorbital rims (FIG. 4A), and a point 4 cm. above the superior attachment point of the external ears along a line normal to the trajectory plane. An extension of this line to the posterior aspect of the skull coincides with alignment of trajectory plane sighting slot 31. Alternatively stated, trajectory plane sighting slot 31 defines a second coordinate of a posterior burr hole site. Therefore, when posterior burr hole localizer 5 is properly positioned on the patient's head, trajectory plane sighting slot 31 invariably defines a region on the trajectory plane for correct catheter insertion; and furthermore, the point of intersection of trajectory plane sighting slot 31 with sagittal plane sighting slot 21 defines the point for optimum posterior burr hole location. The actual trajectory for correct catheter insertion is defined by a straight line from the optimum posterior burr hole location to the anterior target site (FIG. 2). Trajectory plane sighting slot 31 may have a rearward extension, or be otherwise modified, in order to facilitate visualization of the optimum posterior burr hole site by the surgeon or other personnel.

Figure 1B:
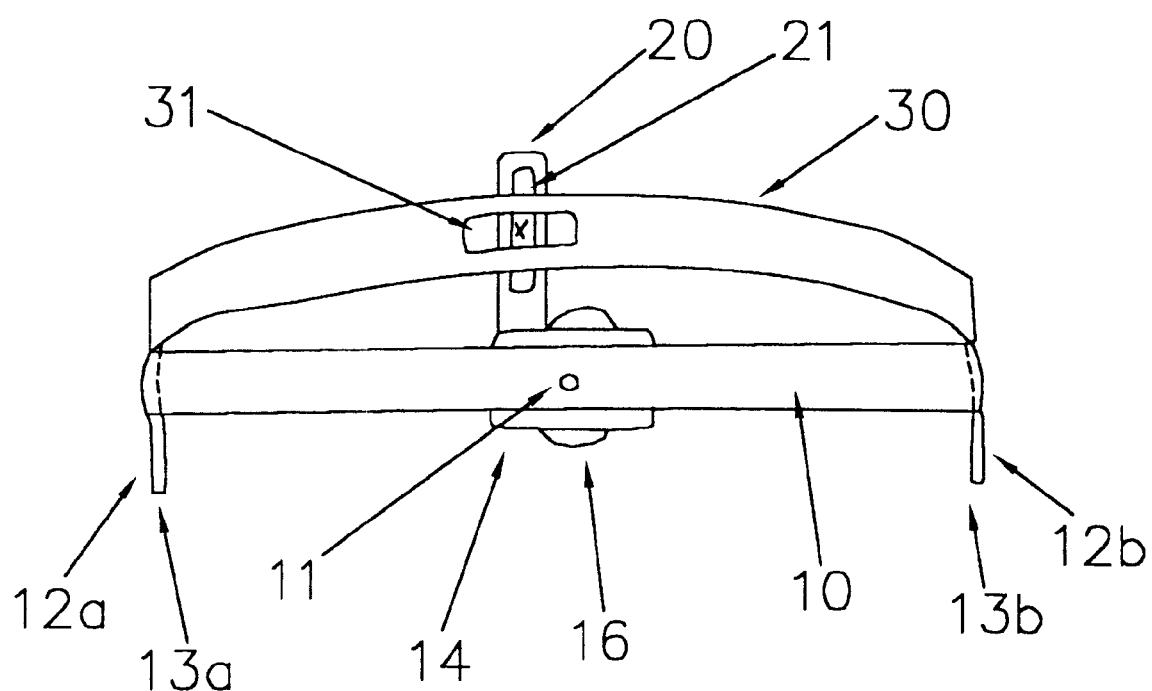
FIG. 1B is a front view of a posterior burr hole localizer.

FIG. 1B is a front view of posterior burr hole localizer 5 according to the invention, showing sagittal plane sighting piece 20, together with trajectory plane aligning piece 30, band tightening control 16, and left and right ear spacers 12a,b, including right and left ear spacer lower edges 13a,b. Posterior burr hole localizer 5 includes an anterior midpoint eyelet 11 located at anterior midpoint 11' of head band 10. Anterior midpoint eyelet 11 is an opening in head band 10 providing access to the skin on the patient's forehead, and anterior midpoint eyelet 11 is invariably located diametrically opposite, or 180 degrees from, posterior midpoint 15. The outline of anterior midpoint eyelet 11 may be of various shapes including, but not limited to substantially circular, triangular, square, etc.; preferably anterior midpoint eyelet 11 is circular or substantially circular in outline. The diameter or width of anterior midpoint eyelet 11 preferably ranges from about 2 mm. to about 10 mm. With posterior burr hole localizer 5 in use, anterior midpoint eyelet 11 is aligned with the anterior midline target site or point (FIGS. 2, 4A).

Figure 1C:
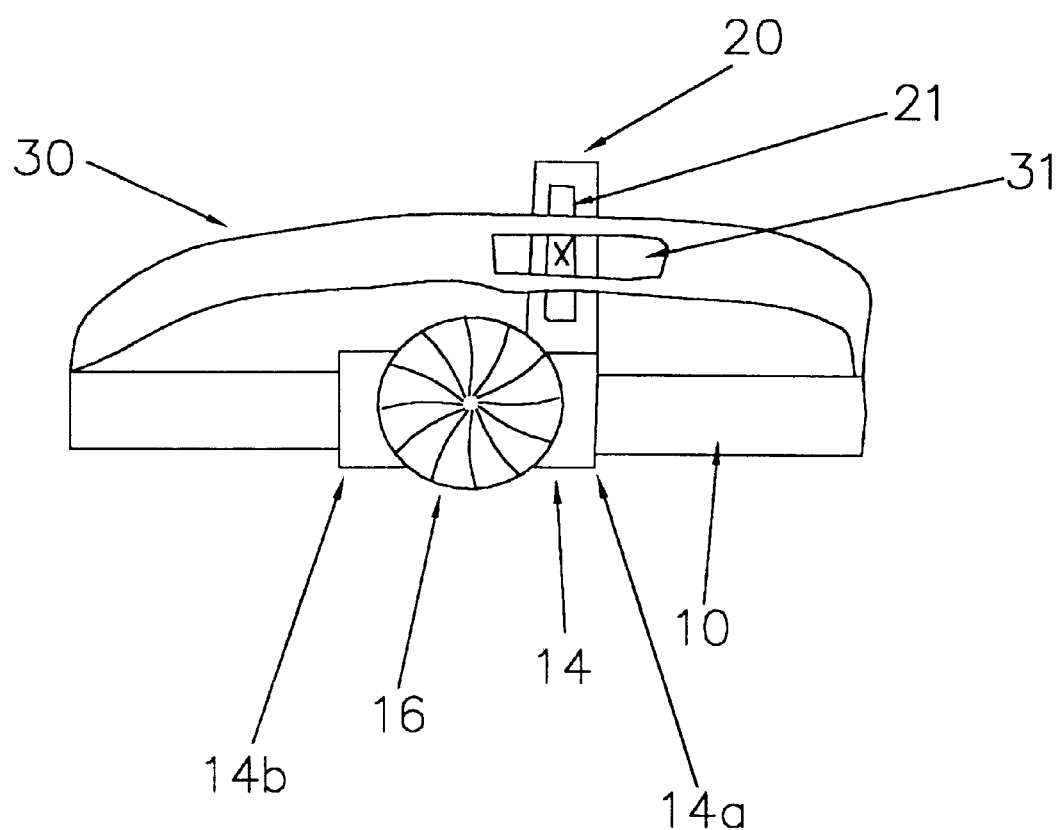
FIG. 1C is a rear view of a posterior burr hole localizer.

FIG. 1C is a rear view of a posterior burr hole localizer according to the invention, showing band constriction unit 14 located at the posterior midpoint 15 (not shown) of head band 10, including band constriction unit right side 14a and band constriction unit left side 14b, together with band tightening control 16. The point of intersection of sagittal plane sighting slot 21 and trajectory plane sighting slot 31, which defines the optimum location for a posterior burr hole site, is marked with an X in FIG. 1C.

Figure 1D:
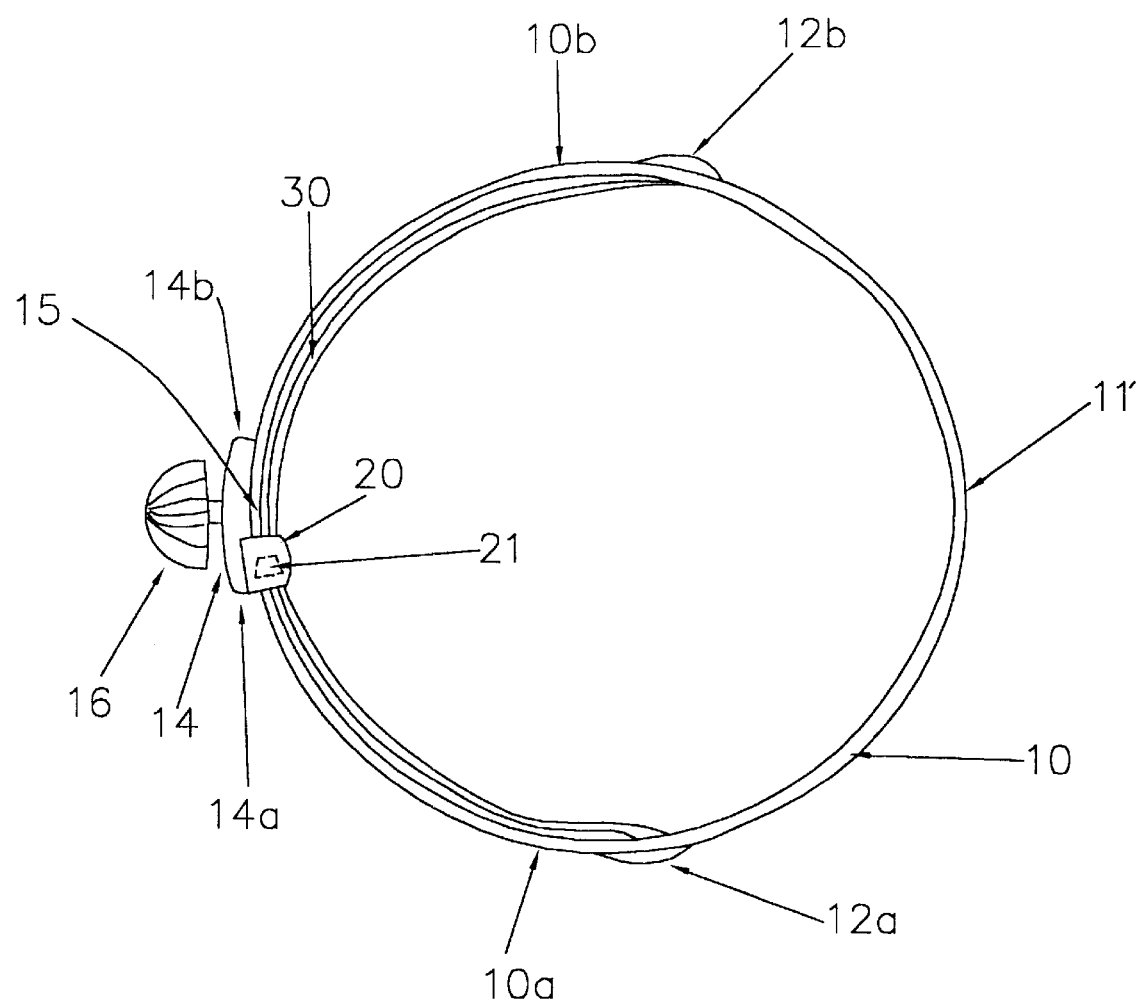
FIG. 1D is a plan view of a posterior burr hole localizer, according to one embodiment of the invention.

FIG. 1D is a plan view of a posterior burr hole localizer, according to the invention, showing the relative locations of anterior midpoint 11' and posterior midpoint 15 of head band 10, these midpoints being diametrically opposed at an angle of 180 degrees to each other. Head band 10 includes head band right side 20a and head band left side 10b. Right and left ear spacers 12a,b are bilaterally disposed on head band 10 at head band right side 10a and head band left side 10b, respectively. Band tightening control 16 is attached centrally to band constriction unit 14 directly behind posterior midpoint 15. When the circumference of head band 10 is adjusted, tightened or loosened, about a patient's head by way of band constriction unit 14 and band tightening control 16, band constriction unit 14 and band tightening control 16 always remain at the posterior midpoint 15 of head band 10. This situation may be achieved by taking up equal lengths of head band right side 10a and head band left side 10b during the tightening process, and conversely by letting out or releasing equal lengths of head band right side 10a and head band left side 10b during the loosening process. The manner in which posterior burr hole localizer 5 of the instant invention may be used to locate the optimal posterior burr hole site is described fully hereinbelow.

FIG. 2 shows the projected catheter trajectory, (seen from below the patients's head) within the trajectory plane, superimposed on an axial CT scan image of a patient prepared prior to burr hole localization and catheter placement. The projected catheter trajectory is portrayed as a dashed line extending from the anterior target point, located midline on the patient's forehead, to the posterior target site for optimum burr hole location, located 3 cm. to the right of the midline. The lateral cerebral ventricle represents the target for catheter placement. Examination of a CT scan may be performed prior to surgery in order to determine whether the patient's ventricular anatomy is compatible with the proposed posterior shunt procedure.

Figure 3A:
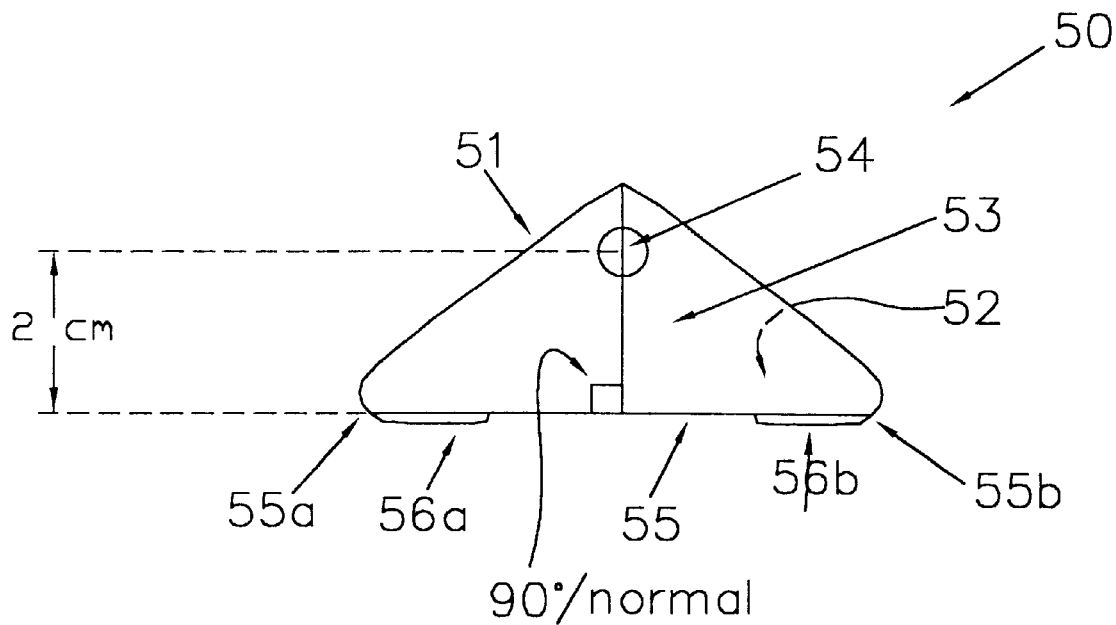
FIG. 3A is a rear view of a frontal target localizing device.

FIG. 3A is a rear view, and FIG. 33 is a rear oblique view, of an anterior or frontal target localizing device 50, according to one preferred embodiment of the invention. Localizing device 50 includes a plate 51 having a first side 52 and a second side 53, a midline localizing unit 54, and basal perimeter 55, including basal perimeter right and left sides 55a, 55b, respectively. Midline localizing unit 54 may be located within plate 51 in the form of an opening traversing plate 51 from first side 52 to second side 53. Localizing device 50 may include right and left orbital rim tabs 56a, 56b, respectively, which may extend from second side 53 of plate 51 flush with basal perimeter 55. According to a preferred embodiment, right and left orbital rim tabs 56a, 56b extend normally (i.e. at an angle of 90 degrees) or substantially normally, away from second side 53 at basal perimeter right and left sides 55a,b. Midline localizing unit 54 is located at the midpoint of localizing device 50, i.e. equidistant from basal perimeter right and left sides 55a,b, and at a distance of about 2 cm. up normal from the basal perimeter 55. According to one embodiment, midline localizing unit 54 may take the form of a circular opening extending through plate 51 from first side 52 to second side 53.

Figure 3B:
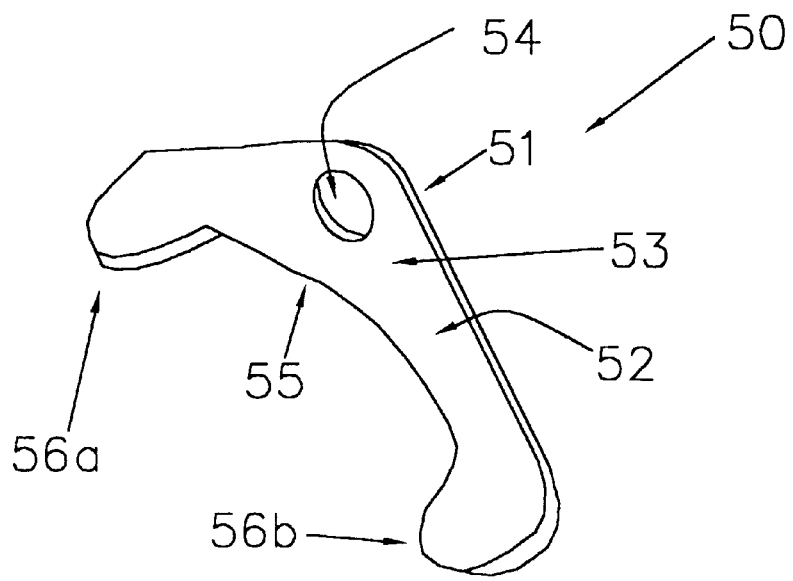
FIG. 3B is a rear oblique view of a frontal target localizing device according to an embodiment of the invention.
Figure 3C:
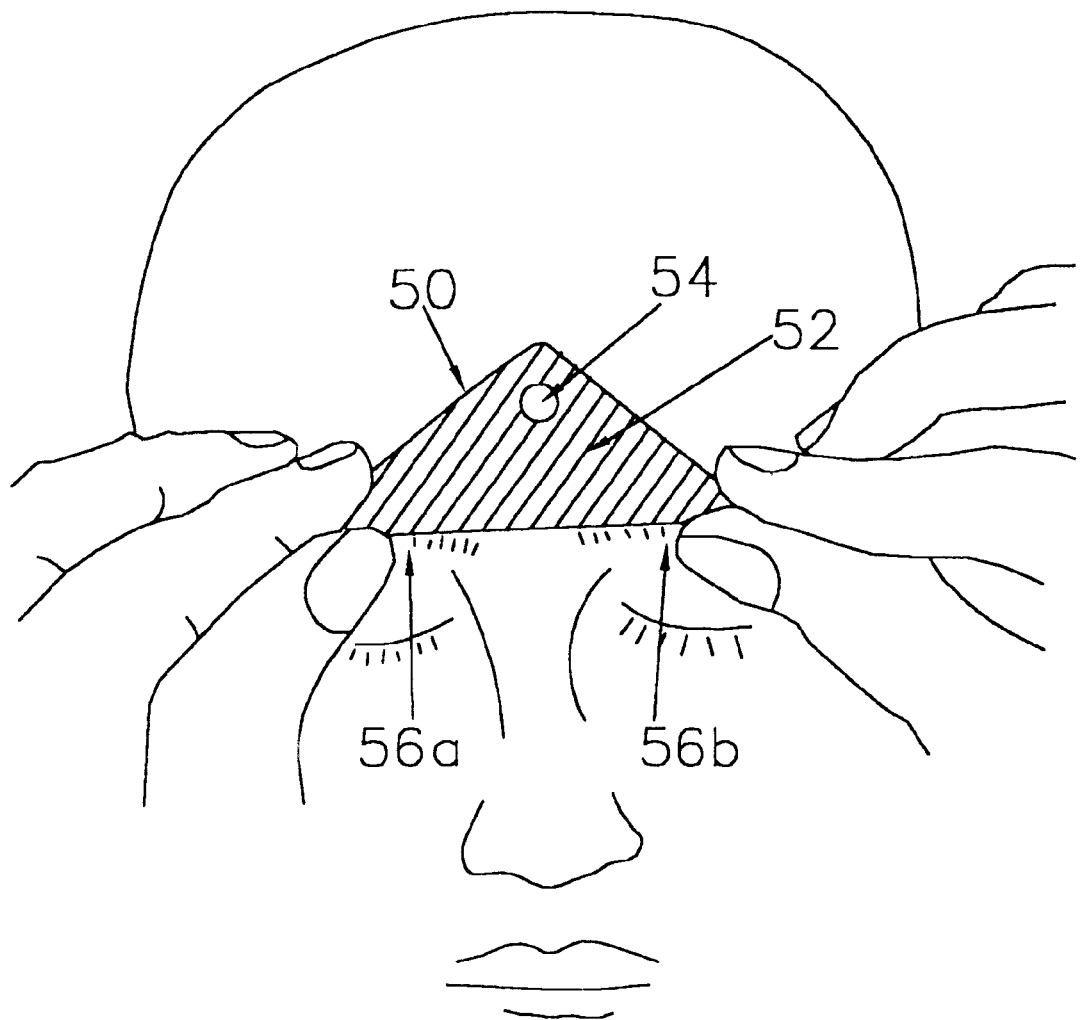
FIG. 3C is a front view of a frontal target localizing device positioned against a patient's forehead, according to another embodiment of the invention.

FIG. 3C shows a frontal target localizing device 50 in use, according to one embodiment of the invention. Right and left orbital rim tabs 56a, 56b are placed flush with the patient's supraorbital rims preliminary to marking a point on the patient's forehead defined by midline localizing unit 54. A point so marked represents the anterior target site for correct catheter trajectory. According to FIG. 3C, midline localizing unit 54 takes the form of a circular opening through which the anterior target point can be marked on the patient's skin.

Although localizing device 50 depicted in FIGS. 3A–3C is substantially triangular in shape, a localizing device 50 embodying the invention, may be of other shapes, including substantially square, or rectangular. Further, a localizing device 50 embodying invention may have fewer, different, or additional elements as compared with the embodiment of FIGS. 3A–3C, provided that a midline localizing unit 54 is located a suitable distance from one or more reference points on localizing device 50.

FIG. 4A is a frontal view of posterior burr hole localizer 5 properly positioned on the patient's head. Properly positioned on the patient's head means that anterior midpoint eyelet 11 is aligned with the anterior target point marked on the patient's forehead, and such that right ear spacer lower edge 13a and left ear spacer lower edge 13b are adjacent to the superior attachment point of the right external ear and the left external ear, respectively. The anterior target site is located at the anterior midline of the patient's forehead, and at a distance about 2 cm. above the supraorbital rims. The anterior target site is represented in FIG. 4A by the dark circle situated within anterior midpoint eyelet 11.

FIG. 4B is a side view of posterior burr hole localizer 5 properly positioned on the patient's head as seen from the right side of the patient. Right ear spacer lower edge 13a is adjacent to the superior attachment point of the right external ear. (Left ear spacer lower edge 13b (not shown) is similarly located adjacent to the superior attachment point of the left external ear.) At the same time, anterior midpoint eyelet 11 (not shown) is aligned with the anterior target point on the patient's forehead. The trajectory plane for correct catheter placement is represented by the dashed line in FIG. 4B, which joins the anterior target point and a point approximately 4 cm. above the superior attachment point of the external ears along a line normal to the trajectory plane. Posterior burr hole localizer 5 is constructed such that, when properly positioned on the patient's head as described hereinabove, trajectory plane aligning piece 30 is aligned with the trajectory plane for correct catheter placement. Furthermore, when posterior burr hole localizer 5 is properly positioned on the patient's head, trajectory plane sighting slot 31 (not shown) defines a region on the posterior of the skull which coincides with the trajectory plane for correct catheter placement. Once posterior burr hole localizer 5 is properly positioned on the patient's head, head band 10 may be constricted by means of band constriction unit 14 in conjunction with band tightening control 16 to affix head band 10 to the patient's head.

Figure 4C:
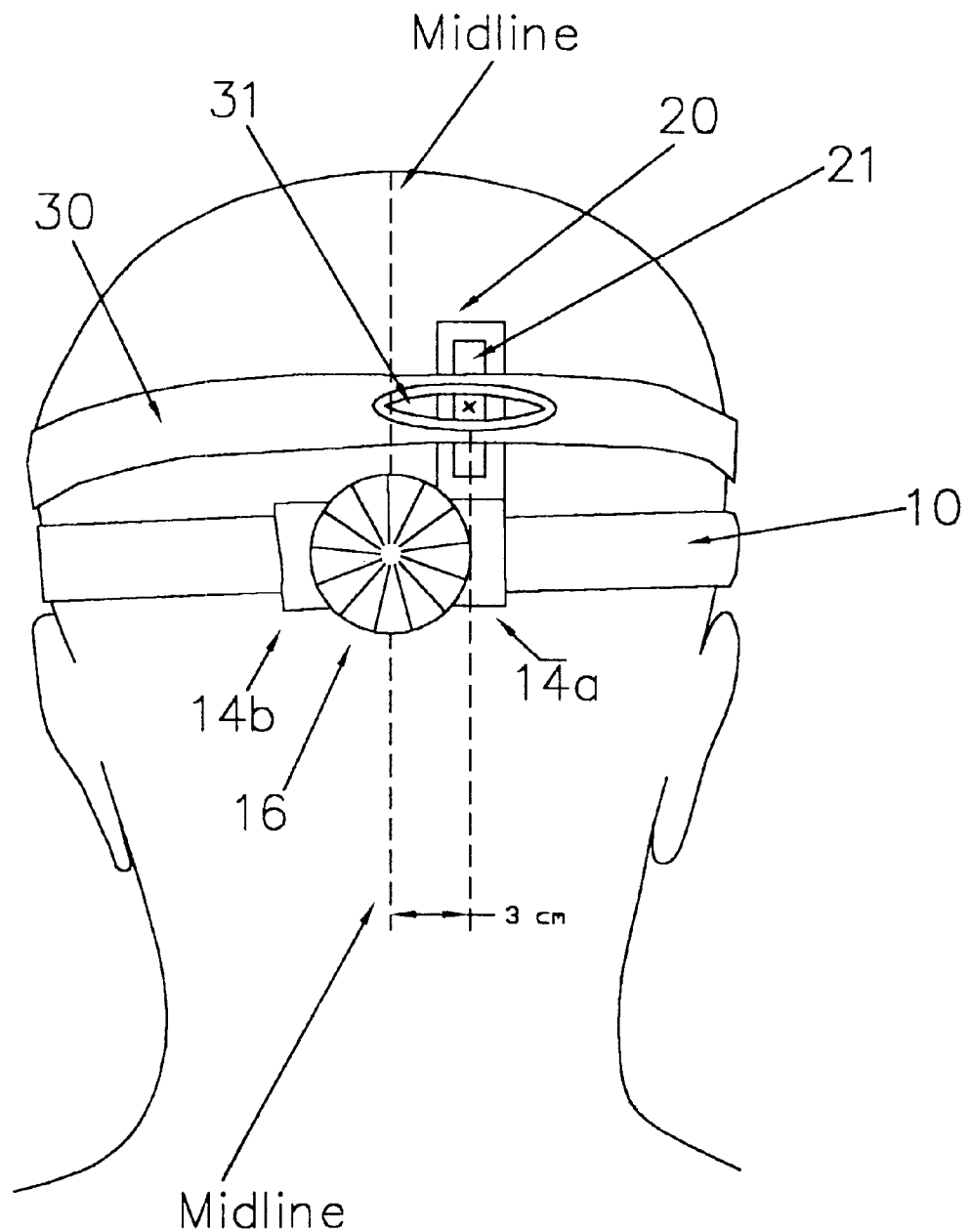
FIG. 4C is a rear view of a posterior burr hole localizer attached to a patient's head showing the intersection of the sagittal plane sighting slot and the trajectory plane sighting slot.

FIG. 4C is a posterior view of posterior burr hole localizer 5 properly positioned on a patient's head. Posterior burr hole localizer 5 includes trajectory plane aligning piece 30 which extends around the back of the patient's head along the trajectory plane for correct catheter placement. Trajectory plane aligning piece 30 includes trajectory plane sighting slot 31 which defines a region on the posterior of the skull which coincides with the trajectory plane for correct catheter placement.

Sagittal plane sighting piece 20 is secured or affixed to band constriction unit right side 14a, and extends in a substantially vertical orientation therefrom. Sagittal plane sighting slot 21 may take the form of a longitudinal slit and defines the sagittal plane at a distance of about 3 cm. to the right of the posterior midline. The intersection of sagittal plane sighting slot 21 and trajectory plane sighting slot 31, marked in FIG. 4C with an X, defines the optimum location for the posterior burr hole site.

Figure 4D:
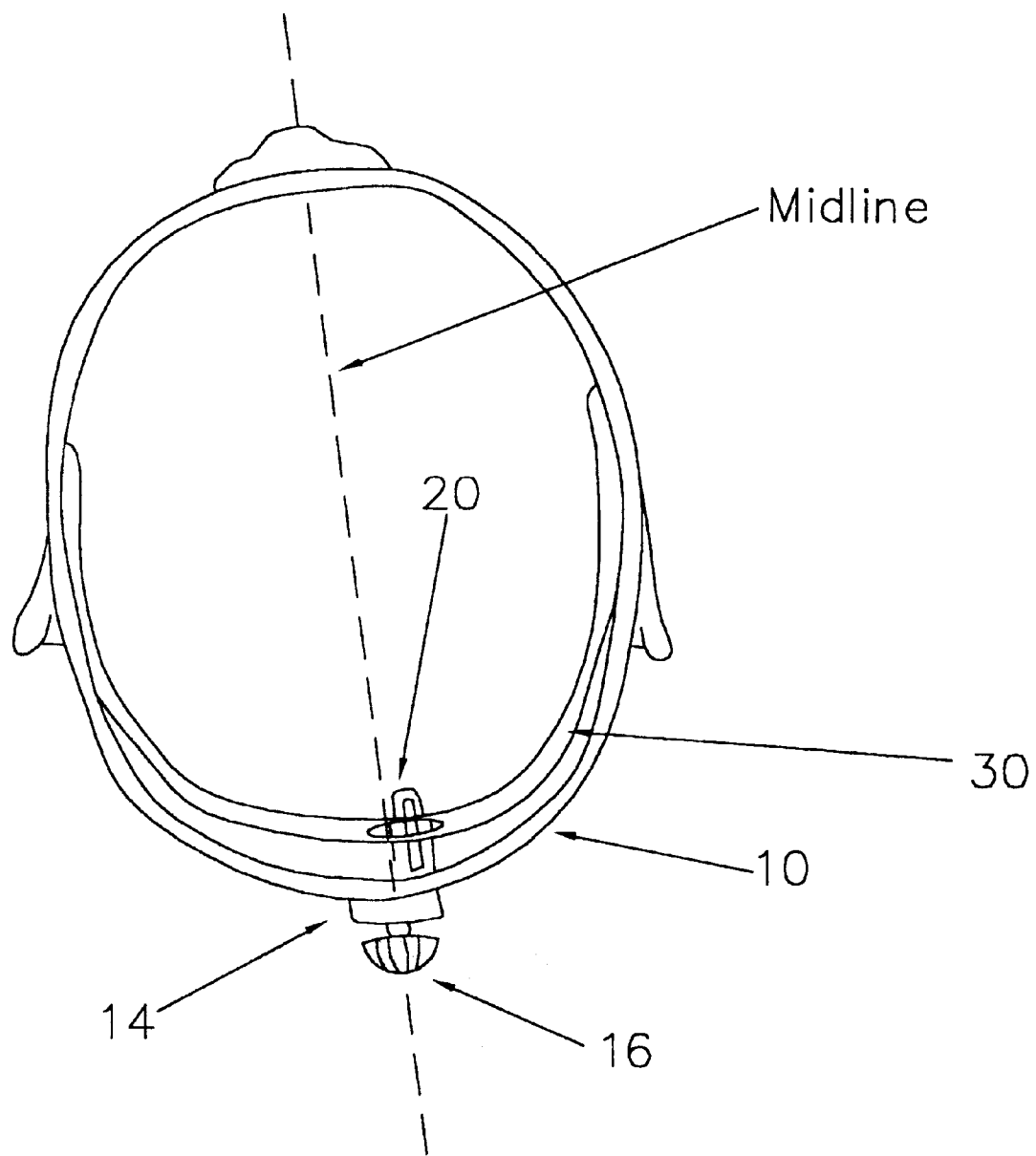
FIG. 4D is a plan view of a posterior burr hole localizer attached to a patient's head showing the mid-line orientation of the band tightening control unit according to one embodiment of the invention.

FIG. 4D is a plan view of posterior burr hole localizer 5 attached to a patient's head according to one embodiment of the invention. FIG. 40 shows the mid-line of the patient's head, which coincides with the orientation of band constriction unit 14 and band tightening control 16 on head band 10. The sagittal plane sighting piece 20 is affixed to band constriction unit right side 14a and is located about 3 cm. to the right of the posterior midline.

Figure 5A:
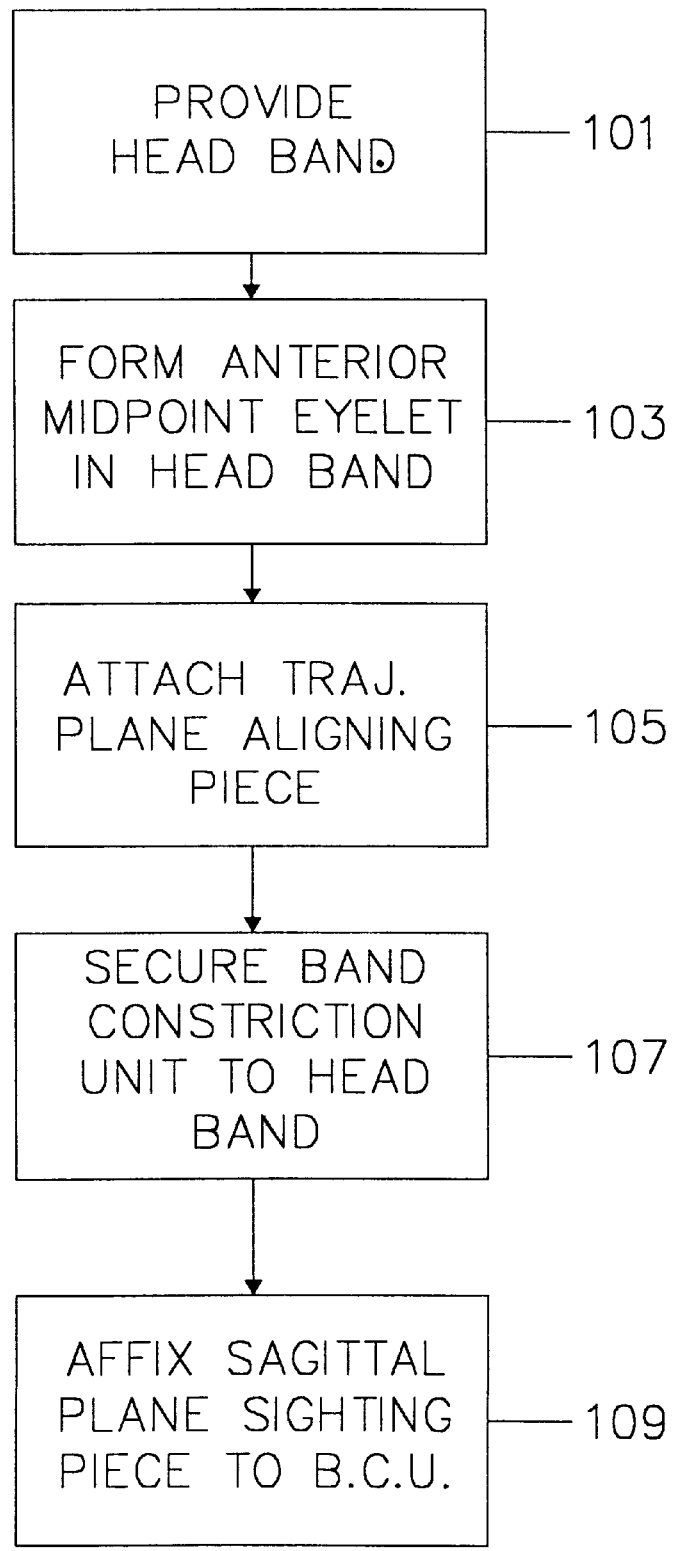
FIG. 5A is a flowchart summarizing the steps in a method for making a posterior burr hole localizer that embodies the invention.

FIG. 5A is a flowchart summarizing the steps in a method for making a posterior burr hole localizer according to one embodiment of the invention. Step 101 involves providing a head band of the posterior burr hole localizer, the head band including an anterior midpoint, a posterior midpoint, and right and left ear spacers. Step 103 involves forming an anterior midpoint eyelet in the anterior midpoint of the head band. Step 105 involves attaching a trajectory plane aligning piece to the head band, the trajectory plane aligning piece including a trajectory plane sighting slot therein. The trajectory plane a sighting slot is in the form of an elongated opening in the latitudinal direction located such that trajectory plane sighting slot is aligned with a trajectory plane for correct catheter placement. The trajectory plane for correct catheter placement being defined by a point approximately 4 cm. above the superior attachment point of each external ear along a line normal to the trajectory plane, and the anterior target point on the patient's forehead. Step 107 involves securing a band constriction unit to the posterior midpoint of the head band. Lastly, step 109 involves affixing a sagittal plane sighting piece to the band constriction unit, wherein the sagittal plane sighting piece includes a sagittal plane sighting slot. The sagittal plane sighting slot may be in the form of an elongated opening within the sagittal plane sighting piece, and oriented in the vertical or longitudinal direction. The sagittal plane sighting slot is arranged on the posterior burr hole localizer such that the sagittal plane sighting slot is located at a distance of about 3 cm. to the right of the posterior midpoint of the head band. In this manner, when the posterior burr hole localizer is properly positioned on a patient's head, the sagittal plane sighting slot is located such that the sagittal plane sighting slot invariably defines the sagittal plane at a distance of about 3 cm. to the right of the posterior midline.

Figure 5B:
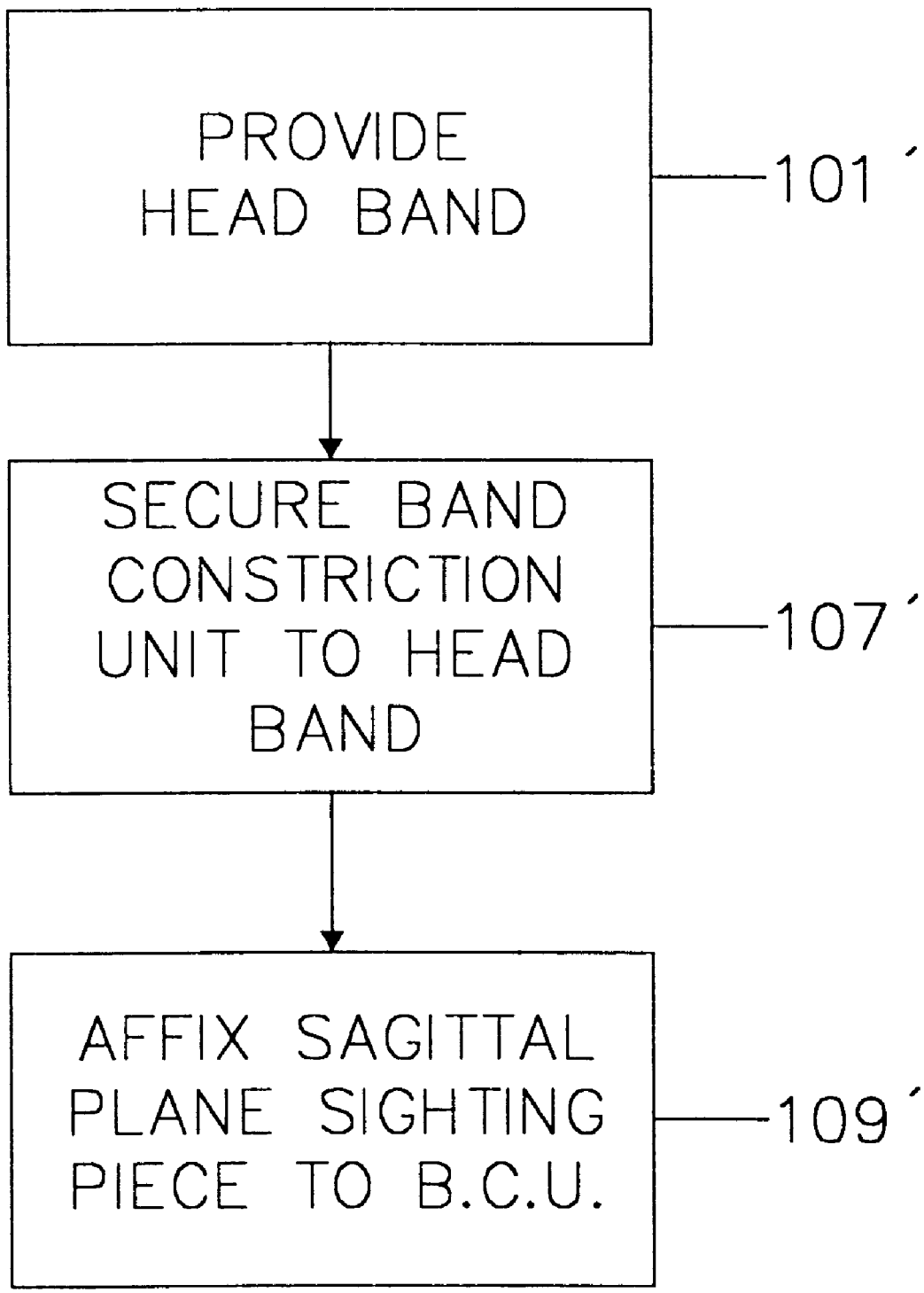
FIG. 5B is a flowchart summarizing the steps in a method for making a posterior burr hole localizer that embodies the invention.

FIG. 5B shows a flowchart summarizing the steps in a method for making a posterior burr hole localizer, according to another embodiment of the invention. Step 101' involves providing a head band, wherein the head band includes an anterior midpoint, a posterior midpoint, and a trajectory plane aligning piece, the trajectory plane aligning piece having a trajectory plane sighting slot located therein. The trajectory plane sighting slot is aligned with the head band of the posterior burr hole localizer such that the trajectory plane sighting slot is invariably aligned with the trajectory plane for correct catheter placement when the posterior burr hole localizer is properly positioned on a patient's head. Step 107' involves securing a band constriction unit to the posterior midpoint of the head band. Finally, step 109' involves affixing a sagittal plane sighting piece to the band constriction unit, wherein the sagittal plane sighting piece includes a sagittal plane sighting slot. The sagittal plane sighting slot is oriented in the vertical direction within the sagittal plane sighting piece, and the sagittal plane sighting piece is positioned on the band constriction unit such that the sagittal plane sighting slot is located at a distance of about 3 cm. to the right of the posterior midpoint of the head band. According to the invention, a band constriction unit may include a band tightening control for tightening and releasing the head band. A method for making a posterior burr hole localizer as described in relation to FIG. 5B may include providing a head band having right and left ear spacers, wherein the right and left ear spacers include right and left ear spacer lower edges, respectively.

Figure 6A:
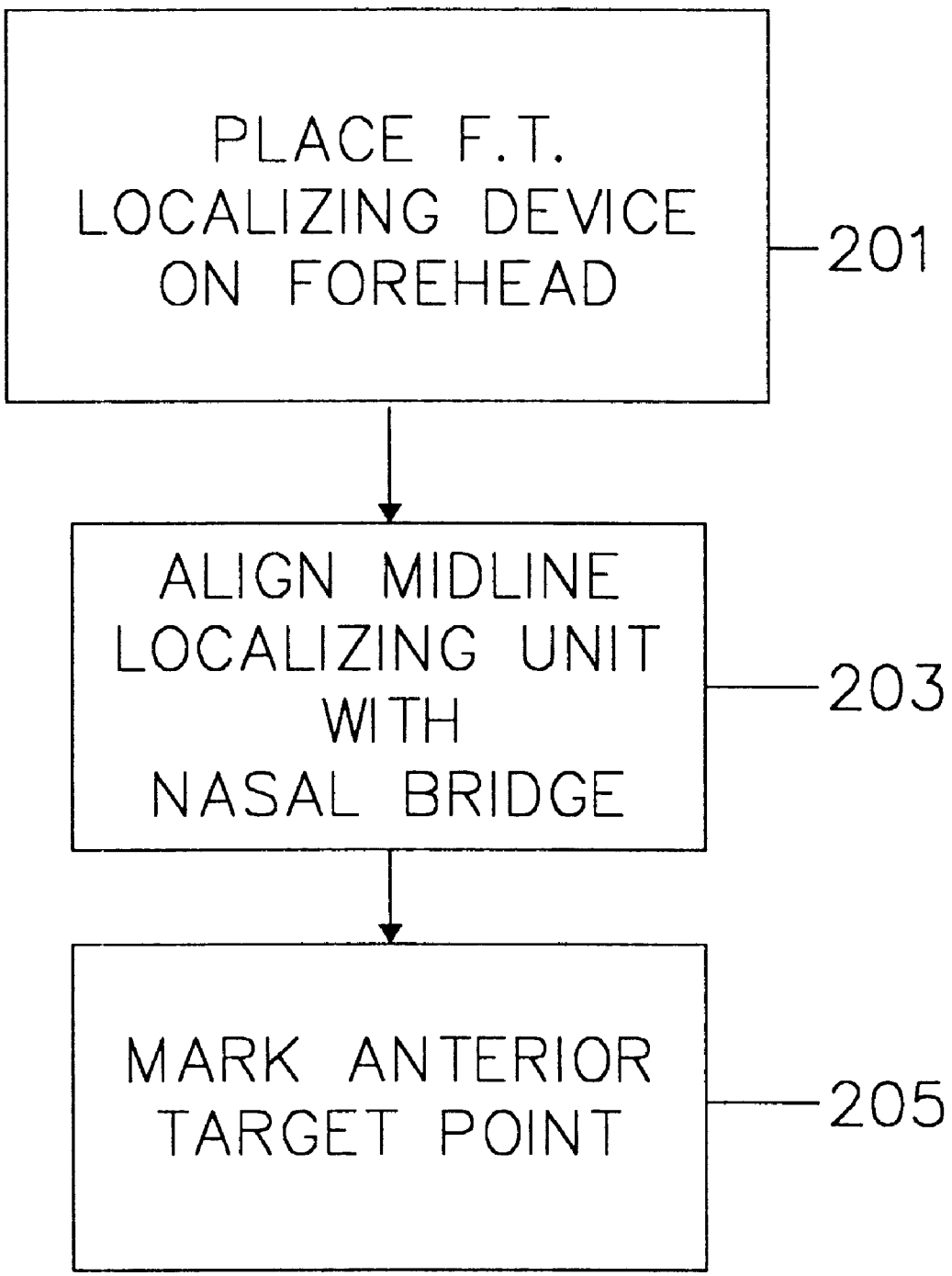
FIG. 6A is a flowchart summarizing a series of steps of a method for locating an anterior target point on a patient's forehead, that embodies the invention.

FIG. 6A shows a flowchart summarizing a series of steps involved in a method for locating an anterior target point on a patient's forehead. Step 201 involves placing a frontal target localizing device against the inferior aspect of the patient's forehead. Step 203 then involves aligning a midline localizing unit of the frontal target localizing device with the anterior midline of the patient's nasal bridge at a distance about 2 cm. above the supraorbital rims of the patient's forehead. Lastly, step 205 involves marking the anterior target point on the patient's forehead at a point defined by the midline localizing unit.

Figure 6B:
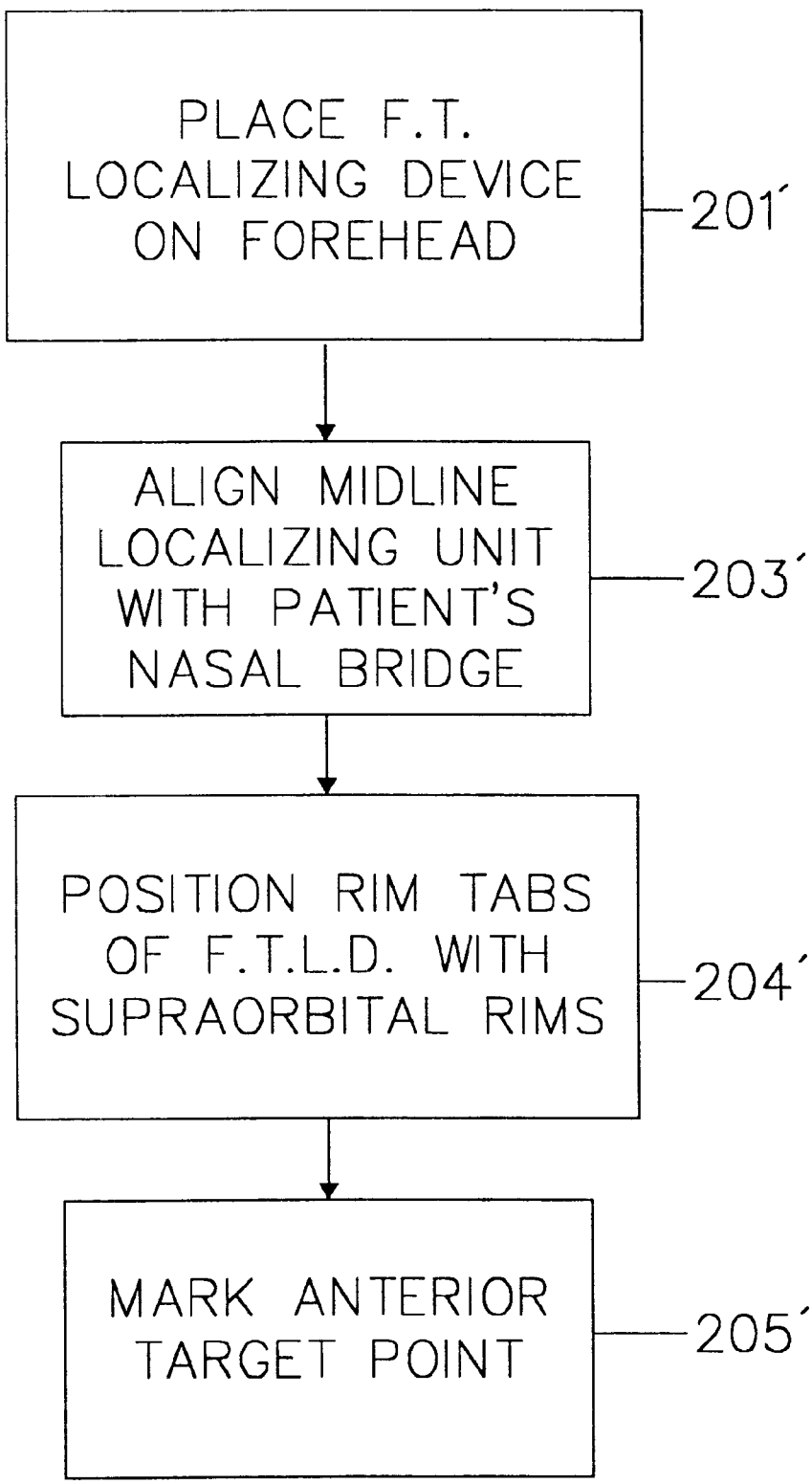
FIG. 6B is a flowchart summarizing a series of steps involved in a method for locating an anterior target point on a patient's forehead that embodies the invention.

FIG. 6B shows a flowchart summarizing a series of steps involved in a method for locating an anterior target point on a patient's forehead. Step 201' involves placing a frontal target localizing device against the inferior aspect of the patient's forehead, the frontal target localizing device including a plate having first and second sides, a midline localizing unit, a basal perimeter, and first and second supraorbital rim tabs extending away from the first side of the plate at the basal perimeter. Step 203' involves aligning the midline localizing unit with the anterior midline of the patient's nasal bridge. Step 204' involves positioning the first and second supraorbital rim tabs such that they are flush, or aligned, with the supraorbital rims of the patient's forehead. Step 204' may be performed coincidentally with aligning the midline localizing unit with the anterior midline of the patient's nasal bridge of step 203'. Finally, step 205' involves marking the anterior target point on the patient's forehead at a point defined by the midline localizing unit.

Figure 7A:
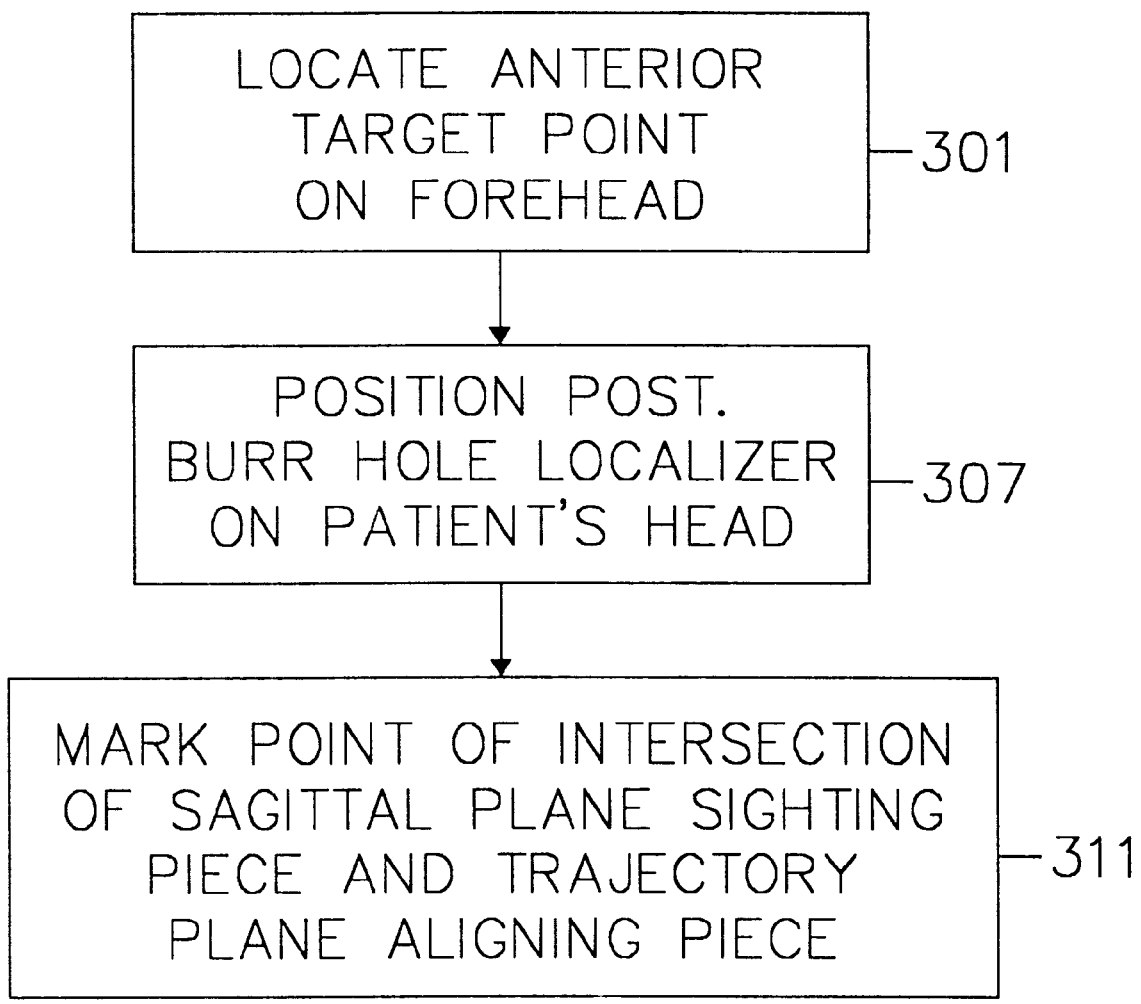
FIG. 7A is a flowchart summarizing steps involved in a method for locating an optimum posterior burr hole site in the occipito-parietal region of a patient's skull that embodies the invention.

FIG. 7A is a flowchart summarizing steps involved in a method for locating an optimum posterior burr hole site in the occipito-parietal region of a patient's skull according to another embodiment of the invention. Step 301 involves locating an anterior target point on the patient's forehead. Step 307 involves positioning a posterior burr hole localizer on the patient's head, wherein the posterior burr hole localizer includes a sagittal plane sighting piece having a sagittal plane sighting slot, and a trajectory plane aligning piece having a trajectory plane sighting slot. The sagittal plane sighting slot and the trajectory plane sighting slot intersect to provide a point of intersection, the point of intersection coinciding with the optimum posterior burr hole site in the occipito-parietal region of the patient's skull. The sagittal plane sighting piece and the trajectory plane aligning piece may be used in concert for mechanical alignment of a marking device, such as a pen, with the point of intersection of the sagittal plane sighting slot and the trajectory plane sighting slot. Lastly, step 311 involves marking the optimum posterior burr hole site at the point of intersection of the sagittal plane sighting slot and the trajectory plane sighting slot. For example, a marking device may be placed through the sagittal plane sighting slot and the trajectory plane sighting slot at their point of intersection to form a mark on the patient's scalp, the mark representing the optimum posterior burr hole site.

Figure 7B:
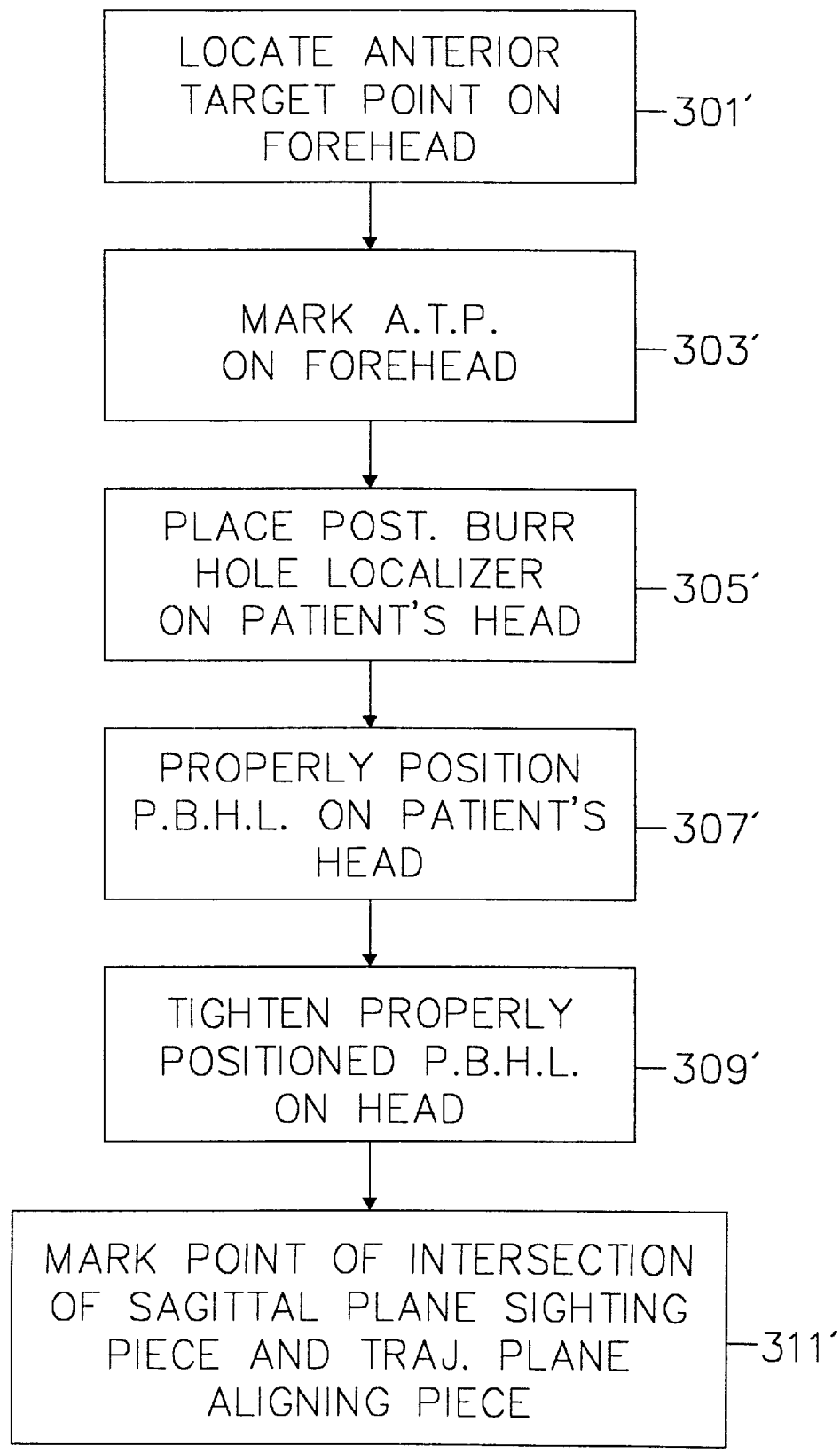
FIG. 7B is a flowchart summarizing steps involved in a method for locating an optimum location for a posterior burr hole that embodies the invention.

FIG. 7B shows a flowchart summarizing steps involved in a method for locating an optimum location for a posterior burr hole, according to another embodiment of the invention. Step 301' involves locating an anterior target point on the patient's forehead. Step 303' involves marking an anterior target point on the patient's forehead. Step 305' involves placing a posterior burr hole localizer on the patient's head. The posterior burr hole localizer includes an anterior midpoint eyelet; right and left ear spacers having a right ear spacer lower edge and a left ear spacer lower edge, respectively; a sagittal plane sighting piece having a sagittal plane sighting slot; and a trajectory plane aligning piece having a trajectory plane sighting slot. The sagittal plane sighting slot and the trajectory plane sighting slot intersect to provide a point of intersection. Step 307' involves properly positioning the posterior burr hole localizer on the patient's head such that the anterior midpoint eyelet is aligned with the anterior target point marked on the patient's forehead, and such that, coincidentally, the right ear spacer lower edge and left ear spacer lower edge are adjacent to the superior attachment point of the right external ear and the left external ear, respectively. The instant method for locating an optimum location for a posterior burr hole, in general, and step 307', in particular, takes advantage of the reliable anatomical relationship between the superior attachment point of the external ears and the cerebral ventricle, whereby the trajectory plane for correct catheter placement is located approximately 4 cm. above the superior attachment point of the external ears along a line normal to the trajectory plane. The trajectory plane corresponding to correct catheter insertion is defined by a straight line joining the anterior target point or site, and a point approximately 4 cm. above the superior attachment point of the external ears along a line normal to the trajectory plane. Optional step 309' involves tightening the properly positioned posterior burr hole localizer on the patient's head. The sagittal plane sighting piece and the trajectory plane aligning piece may be used in concert for mechanical alignment of a marking device, such as a pen, with the point of intersection of the sagittal plane sighting slot and the trajectory plane sighting slot. Finally, step 311' involves marking the point of intersection of the sagittal plane sighting slot and the trajectory plane sighting slot to locate the optimum location for the posterior burr hole. A marking device may be placed through the sagittal plane sighting slot and the trajectory plane sighting slot at their point of intersection to form a mark on the patient's scalp, the mark representing the optimum posterior burr hole site.

Figure 8A:
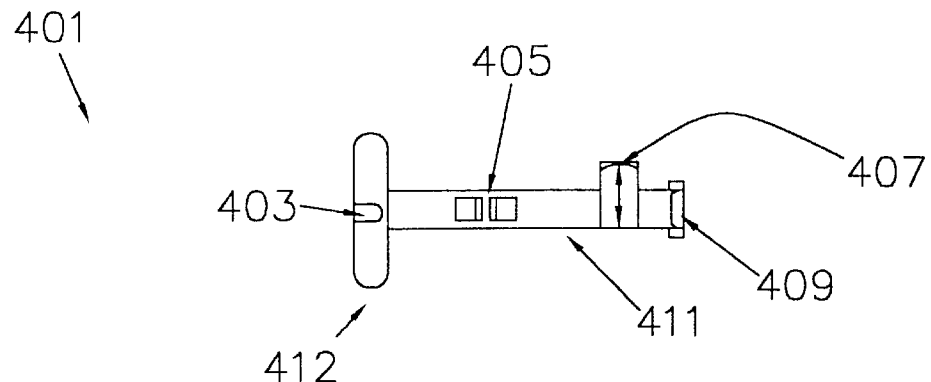
FIG. 8A shows a plan view.
Figure 8B:
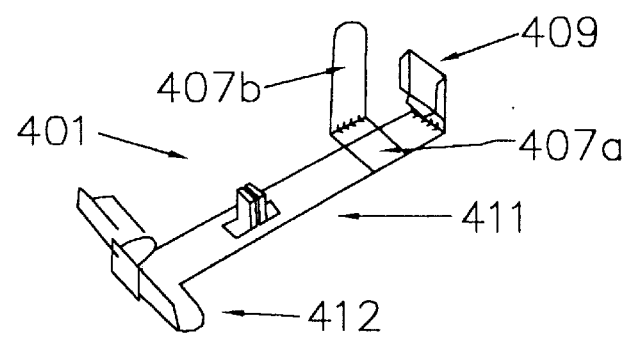
FIGS. 8B and 8C show perspective views of a storage rack for holding a posterior burr hole localizer, according to another embodiment of the invention.
Figure 8C:
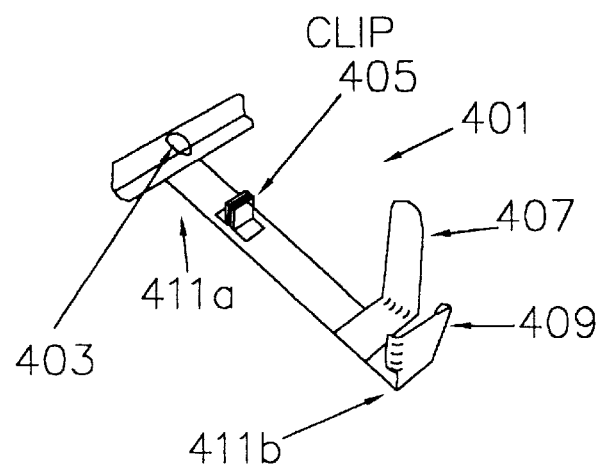

FIG. 8A shows a plan view, and FIGS. 8B and 8C show perspective views of a storage rack 401 for holding a posterior burr hole localizer, according to one embodiment of the invention. Rack 401 is substantially T-shaped having elongate member 411 with first end 411*a* and second end 411*b*. A cross piece 412 is attached to elongate member 411 at first end 411*a* substantially at right angles, or perpendicularly, thereto. Cross piece 412 includes an extension in the form of eyelet docking post 403 which extends along the longitudinal axis of elongate member 411 towards second end 411*b*. Eyelet docking post 403 has a length of from about 2 mm. to about 10 mm., and a diameter ranging from about 2 mm. to about 10 mm. In any event, eyelet docking post 403 has a diameter at least slightly less than the diameter or width of anterior midpoint eyelet 11. Eyelet docking post 403 is of suitable dimensions and location with respect to storage rack 401 to allow the facile docking of anterior midpoint eyelet 11 of head band 10. The docking of anterior midpoint eyelet 11 in eyelet docking post 403 is required for proper stowage of localizer 5 in storage rack 401. A clip 405 is attached to elongate member 411 for the purpose of holding anterior target localizing device 50. A knob holder 409 is attached to elongate member 411 at second end 411*b*. Knob holder 409 is for accommodating or holding a band tightening knob or band tightening control 16. A sagittal plane sighting slot alignment indicator 407 is attached to elongate member 411 at a point on elongate member 411 between knob holder 409 and clip 405. Sagittal plane sighting slot alignment indicator 407 includes a foot portion 407*a* and a shank portion 407*b*. With posterior burr hole localizer 5 properly stowed in storage rack 401, sagittal plane sighting slot 21 should be perfectly aligned with sagittal plane sighting slot alignment indicator 407. If this is not the case, localizer 5 should not be used. Thus, storage rack 401 also functions as an alignment checking tool.

The posterior burr hole localizer of the instant invention has been described herein primarily with respect to treatment of adult humans. The posterior burr hole localizer has been found to be capable of accommodating a number of adult patients with a broad range of head sizes. For the treatment of children, a smaller version of the posterior burr hole localizer (similarly including an adjustable head band) is envisioned and is contemplated as being within the scope of the posterior burr hole localizer device, and methods therefor, as claimed hereinbelow.

The foregoing embodiments are merely exemplary and are not to be construed as limiting the present invention. The present teaching can be readily applied to other types of apparatus. The description of the present invention is intended to be illustrative, and not to limit the scope of the claims. Many alternatives, modifications, and variations will be apparent to those skilled in the art.

What is claimed is:

1. A posterior burr hole localizer for locating a posterior burr hole site on a patient's head, comprising:

a head band including an anterior midpoint locating device at an anterior midpoint of the head band;

a sagittal plane aligning piece attached to said head band for determining a location of a first coordinate of an optimum posterior burr hole site on a patient's head;

a trajectory plane aligning piece attached to said head band for determining a location of a second coordinate of an optimum posterior burr hole site on the patient's head, and a posterior burr hole locating device attached to the head band and configured to indicate a location of an optimum posterior burr hole site on a patient's head.

2. The posterior burr hole localizer of claim 1, wherein said posterior burr hole locating device includes a sagittal plane sighting slot formed on the sagittal plane aligning piece, and wherein said sagittal plane sighting slot defines the location of the first coordinate of the optimum posterior burr hole site.

3. The posterior burr hole localizer as claimed in claim 1, wherein the sagittal plane aligning piece is attached to the headband such that the sagittal plane aligning piece defines said first coordinate so that the first coordinate lies in a sagittal plane located between approximately 1.5 and 4.5 cm to the right of a posterior midpoint of a patient's head when the head band is properly positioned on the patient's head.

4. The posterior burr hole localizer of claim 3, wherein the trajectory plane aligning piece is attached to the headband such that the trajectory plane aligning piece defines the second coordinate so that the second coordinate lies in a trajectory plane passing through an anterior target point on a patient's forehead and points approximately 2.5–5.0 cm above superior attachment points of the patient's right and left external ears along lines extending normal to the trajectory plane.

5. The posterior burr hole localizer of claim 1, wherein the trajectory plane aligning piece is attached to the headband such that the trajectory plane aligning piece defines the second coordinate so that the second coordinate lies in a trajectory plane passing through an anterior target point on a patient's forehead and points approximately 2.5–5.0 cm above superior attachment points of the patient's right and left external ears along lines extending normal to the trajectory plane.

6. The posterior burr hole localizer of claim 1, wherein the posterior burr hole locating device includes a trajectory plane sighting slot on the trajectory plane aligning piece, and wherein said trajectory plane sighting slot defines the location of the second coordinate of the optimum posterior burr hole site.

7. The posterior burr hole localizer of claim 6, wherein said posterior burr hole locating device includes a sagittal plane sighting slot on the sagittal plane sighting slot, and wherein said sagittal plane sighting slot defines the location of the first coordinate of the optimum position burr hole site.

8. The posterior burr hole localizer of claim 1, further comprising right and left ear spacers attached to the head band.

9. The posterior burr hole localizer of claim 8, wherein the right and left ear spacers comprise lower edges that are configured to abut superior attachment points of a patient's right and left external ears, respectively, when the head band is properly positioned on the patient's head.

10. The posterior burr hole localizer of claim 1, further comprising a band tightening unit for varying a circumference of the head band.

11. The posterior burr hole localizer of claim 1, further comprising an anterior target point locater on an anterior midpoint of the headband.

12. A posterior burr hole localizer to be properly positioned on the head of a patient for determining an optimum location for a posterior burr hole site on the patient's head, comprising:

a head band including an anterior midpoint eyelet located at an anterior midpoint of the head band such that the eyelet aligns with an anterior target site on a patient's head when the head band is properly positioned on the patient's head;

right and left ear spacers attached to the head band and having respective right and left ear spacer lower edges, said right and left ear spacer lower edges being located adjacent to superior attachment points of right and left external ears of the patient, respectively, when the head band is properly positioned on the patient's head;

a band constriction unit for varying a circumference of the head band, the band constriction unit being located adjacent a posterior midpoint of the patient's head when the head band is properly positioned on the patient's head;

a trajectory plane aligning piece attached to said head band, said trajectory plane aligning piece having a trajectory plane sighting slot, said trajectory plane sighting slot defining a region on a trajectory plane for correct catheter placement; and a sagittal plane sighting piece attached to one of said head band and said band constriction unit, said sagittal plane sighting piece including a sagittal plane sighting slot that defines a sagittal plane located between approximately 1.5 and 3.5 cm to the right of a posterior midline of the patient's head, and wherein said sagittal plane sighting slot intersects with said trajectory plane sighting slot to provide a point of intersection that defines the optimum location for a posterior burr hole site.

13. The posterior burr hole localizer as claimed in claim 12, wherein a straight line between said point of intersection and said anterior midpoint eyelet define a trajectory for correct catheter insertion.

14. The posterior burr hole localizer of claim 12, wherein said trajectory plane for correct catheter placement passes through the anterior target site and points located approximately 2.5–5.0 cm above the superior attachment points of a patient's right and left ears along lines extending normal to the trajectory plane.

15. A posterior burr hole localizer for locating a posterior burr hole on a patient's head, comprising:

band means for attaching the burr hole localizer to a patient's head;

sagittal plane aligning means, attached to the band means, for determining a location of a first coordinate of an optimum posterior burr hole site on a patient's head;

trajectory plane means, attached to the band means, for determining a second coordinate of an optimum posterior burr hole site on the patient's head; and indicating means for indicating an optimum posterior burr hole site.

16. The posterior burr hole localizer of claim 15, wherein the sagittal plane aligning means is configured to determine the first coordinate of the posterior burr hole site such that the burr hole site lies in a sagittal plane located approximately 1.5–4.5 cm to the right of a posterior midpoint of a patient's head.

17. The posterior burr hole localizer of claim 15, wherein the trajectory plane means is configured to determine the second coordinate of the posterior burr hole site such that it lies in a trajectory plane passing through an anterior target point on a patient's forehead, and points approximately 2.5–5.0 cm above superior attachment points of a patient's left and right ears along lines extending normal to the trajectory plane.

18. The posterior burr hole localizer of claim 15, further comprising ear spacing means for spacing the band means above superior attachment points of a patient's ears.

19. The posterior burr hole localizer of claim 15, further comprising tightening means for firmly affixing the band means to a patient's forehead.

20. The posterior burr hole localizer of claim 15, further comprising means for locating an anterior midpoint of a patient's forehead.

\* \* \* \* \*